US008993767B2

(12) United States Patent
Dalko et al.

(10) Patent No.: US 8,993,767 B2
(45) Date of Patent: Mar. 31, 2015

(54) MULTIPHOTON ACTIVABLE QUINOLINE DERIVATIVES, THEIR PREPARATION AND THEIR USES

(75) Inventors: Peter Dalko, Orsay (FR); Morgane Petit, Paris (FR); David Ogden, Rambouillet (FR); Francine Acher, Vaucresson (FR)

(73) Assignee: Centre National de la Recherche Scientifique, Paris (FR)

( * ) Notice: Subject to any disclaimer, the term of this patent is extended or adjusted under 35 U.S.C. 154(b) by 128 days.

(21) Appl. No.: 13/521,936

(22) PCT Filed: Jan. 12, 2011

(86) PCT No.: PCT/IB2011/000207
§ 371 (c)(1),
(2), (4) Date: Nov. 30, 2012

(87) PCT Pub. No.: WO2011/086469
PCT Pub. Date: Jul. 21, 2011

(65) Prior Publication Data
US 2013/0116281 A1 May 9, 2013

(30) Foreign Application Priority Data
Jan. 12, 2010 (EP) .................................. 10290011

(51) Int. Cl.
*C07D 215/38* (2006.01)
*C09B 57/00* (2006.01)
*B82Y 20/00* (2011.01)
*C07D 215/12* (2006.01)
*C07D 215/48* (2006.01)

(52) U.S. Cl.
CPC .............. *C09B 57/008* (2013.01); *B82Y 20/00* (2013.01); *C07D 215/12* (2013.01); *C07D 215/38* (2013.01); *C07D 215/48* (2013.01)
USPC ............................ 546/156; 546/159; 546/162

(58) Field of Classification Search
CPC ............................ C07D 215/12; C07D 215/40
USPC ........................................ 546/156, 159, 162
See application file for complete search history.

(56) References Cited

PUBLICATIONS

Katan, Effects of (Multi)branhing of Dipolar Chromophores Photophysical Properties and Two-Proton Absorption, Journal of Physical Chemistry, 109, pp. 3024-3037, 2005.
Droumaguet, Towards "Smart" Multiphoton Fluorophores: Strongly Solvatochromic Probes for Two-Photon Sensing of Micropolarity, Chemical Communications, pp. 2802-2804, 2005.
Mongin, Synthesis and Two-Photon Absorption of Highly Soluble Three-Branched Fluorenylene-Vinylene Derivatives, Tetrahedron Letters, 44, pp. 8121-8125, 2003.
Parent, New Chromophores from Click Chemistry for Two-Photon Absorption and Tuneable Photoluminescence, Chemical Communications, pp. 2029-2031, 2005.

*Primary Examiner* — D M Seaman
(74) *Attorney, Agent, or Firm* — Morgan, Lewis & Bockius LLP

(57) ABSTRACT

The present invention relates to multiphoton activable organic compounds responding to the following formula (I). The present invention also relates to a method of synthesizing the compounds of the invention, to an aqueous solution comprising at least one compound of the invention, and to their specific uses. The present invention also concerns a method of liberating organic ligands, said method involving the step of irradiating a compound according to the invention.

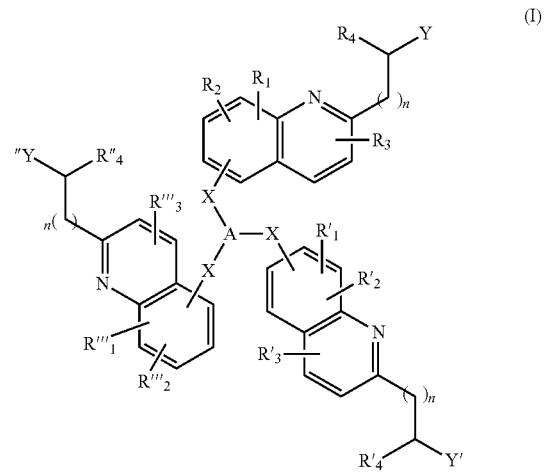

11 Claims, 1 Drawing Sheet

MULTIPHOTON ACTIVABLE QUINOLINE DERIVATIVES, THEIR PREPARATION AND THEIR USES

RELATED APPLICATIONS

Figure 1:
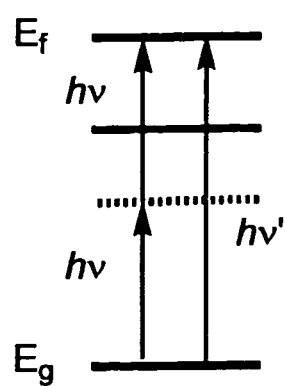

The present application is a U.S. National Phase Application of International Application No. PCT/IB2011/000207 (filed Jan. 12, 2011) which claims priority to European Application No. 10290011.5 (filed Jan. 12, 2010) which are hereby incorporated by reference in their entirety.

The present invention relates to multiphoton activable organic compounds, to a method of synthesizing these compounds, to an aqueous solution comprising at least one compound of the invention, and to their specific uses. The present invention also concerns a method of liberating organic ligands, said method involving the step of irradiating a compound of the invention.

The importance of the design and synthesis of novel organic multiphoton active materials and their application in nonlinear photonics is recognized as a central paradigm in many areas of research and technology. The substrates range in size from small organic chromophores to dendrimers, polymers and metal-containing compounds. The rapidly expanding field of multiphoton excited processes is mainly promoted by the great potential of various applications utilizing efficient multiphoton excitation. Some examples are: frequency up-conversion lasing; optical power limiting, frequency up-conversion imaging and microscopy; optical microfabrication; optical data storage and processing; and multiphoton associated biological and medical applications.

Light activable conjugates (caged compounds) offer great flexibility in initiating physical, chemical or biochemical events at the nano-scale—hundreds of nanometers—with good time resolution, spatial and time-control (Bülher et al., Helv. Chim. Acta, 2004, 87, 620-659).

The features of high spatial confinement of multiphoton interactions and the penetrating capability of a focused laser beam can effectively be used to create three-dimensional (3D) microstructures or to fabricate micro-machines with a sub-diffraction limit spatial resolution. The emergence of the 3D microfabrication is one of the achievements of multiphoton-based application techniques. This technique is essentially a multiphoton interaction-based 3D photolithography (Zhou et al., Science, 2002, 296, 1106; Maruo et al., Laser Photonics Rev., 2008, 2, 100).

In microfabrication, the multiphoton-initiated chemistry is used to define 3D structures, and more particularly 3D microstructures, including microchannels, micropumps, cantilevers, plasmonic devices, and photonic crystals, said photonic crystals being used in microfluidic, biomedical, micro-electromechanical, and photonic systems.

The modification of the chemical and physicochemical characteristics of a material can be achieved by a two-photon process in solution, in a gel and in a monolayer, and could be monitored by an adequate methodology such as the dye decoration procedure (Alvarez et al., Adv. Materials, 2008, 20, 4563-4567). This well-defined lithography by using two-photon deprotection provides access to near-field induced structuring with ultimate spatial resolution. The presence of free functional groups after deprotection promises further functionalization not only by physisorption but also by covalent attachment of various reactive species (e.g. biomolecules, functional polymers and nano-objects). Thus, two-photon induced structured surface, in particular in connection with near field localization, may turn out to be the key to ultra-high resolution photolithography.

Other applications concern the photochemical external control of in vivo biological process by light, which is becoming increasingly important in cutting edge biological research. Indeed, photocleavable reagents capable of releasing photolabile compounds quickly upon irradiation are potentially valuable tools, notably for study of biological phenomena. In this case, light-responsive compounds comprise a caging moiety that is linked to a biologically active moiety, said compounds being able to release the active moiety under irradiation. The photorelease compounds, which are temporarily inactive (before the irradiation) can be used therefore to deliver active moieties, like peptides, proteins, nucleic acids or effector molecules ("small molecules"), where their activity is required. Hence, the photolabile protecting groups are removed with light, and the "small molecules" are switched from an inactive state to an active state.

Light irradiation is potentially a non-invasive methodology that results in minimal perturbation of cellular processes. In the case of photolabile precursors that render the biological effect of the released ligand inert, the photolysis will restore the biological activity. These caged compounds were used extensively for the investigation of kinetics and cellular mechanisms by releasing low molecular weight regulators including neurotransmitters, phosphatidic acid, nitric oxide, metal ions such as $Ca^{2+}$, and more recently for processes such as gene regulation (Ellis-Davies, Chem. Rev., 2008, 108, 1603-1613; Lipp et al., J. Physiol., 1998, 508, 801-901; Lindegger et al., J. Physiol, 2005, 565, 801-813; Ellis-Davies, Cell Calcium, 2006, 39, 471-473; Takano et al., Cell Calcium, 2007, 41, 503-504; Brown et al., Method Enzymol, 1998, 201, 356-380; DelPrincipe et al., Cell Calcium, 1999, 28, 85-91; Momotake et al., Nat. Methods, 2006, 3, 35-40).

Theoretical Basis of Two-Photon Absorption:

The two-photon activation (2PA) in photolysis results from the quasi-simultaneous absorption of two photons, initiating a reaction sequence resulting in the release of a ligand. The simultaneous absorption of two quanta of energy was predicted theoretically (Göppert, Naturwissenachaften, 1929, 17, 932; Göppert-Mayer, Ann. Phys., 1931, 9, 273-294), and was observed experimentally shortly after the discovery of the high intensity lasers in the 1960s (Peticolas, Ann. Rev. Phys. Chem., 1967, 18, 233-260). Based on the quantum theory of radiation, the theory of Göppert-Mayer predicts the simultaneous absorption of two or more photons via intermediate states between a lower and a higher energy level of an atom or a molecule. In a 2PA process, such transition can be represented as depicted in FIG. 1, where the intermediate state is schematically represented by a dashed line level between two real states of the molecule. The molecular transition between the two real states can be visualized as a "two-step" event. In the first step, one photon is absorbed while the molecule leaves its initial state $E_g$ to be excited to an intermediate state. In the second step, another photon will be absorbed while the same molecule completes its transition from the intermediate state to the final real state $E_f$. These transitions occur within $10^{-16}$ second timescale and appear as a single elementary process.

The major feature distinguishing single-photon absorption (1PA) from 2PA is the fact that the rate of energy absorption (light) is as a function of incident intensity (Belfield et al., Org. Lett., 1999, 1, 1575). As the probability to populate the intermediate state(s) is infinitely low, the simultaneous absorption of two or more photons requires high peak power, which is now available from commercial ultrafast-pulsed lasers. In 1PA the rate of light absorption is directly proportional to the incident intensity, whereas in 2PA the rate is proportional to the square of the incident intensity. This nonlinear dependence has substantial implications. For example, in a medium containing one-photon absorbing chromophores, significant absorption occurs all along the path of a focused light beam of suitable wavelength. This can lead to the activation of the caged substrate along the beam resulting in uncontrolled biological responses. In two- or multi-photon absorption, negligible absorption occurs except in the immediate vicinity of the focal point of a light beam of appropriate energy, provided that the chromophore does not absorb at this wavelength (Denk et al., Science, 1990, 248, 73).

In addition, the use of a longer wavelength excitation source affords further advantages not feasible using conventional UV or visible techniques, for example, about two-fold deeper penetration of the excitation beam and much reduced excitation by scattered photons (Oheim et al., J. Neuroscience Methods, 2001, 111, 29-37).

In many applications, the caged compounds currently in use for two-photon photolysis are derived from 1PA cages. These compounds are polar molecules in which a large change in dipole moment (>10 D) occurs under excitation of the ground to an excited state (Birge et al., Molecular Electronics, 1997, Chapter 15): the absorption cross-section is essentially a function of this transition dipole moment (Albota et al., Science, 1988, 281, 1653-1656). The rational design of these compounds is difficult because of the lack of data and of a verified theoretical model for the structure correlation with 1PA or 2PA photolysis. A common strategy used to improve the 2PA cross-section is to increase the polarizability of the compound by increasing the length of the π-conjugation, or by adding <<antennas>> that harvest light more efficiently and transfer the absorbed energy to the cage by Förster type dipole coupling (Förster T., Ann. Physik., 1948, 437, 55).

Nitrobenzyl compounds (NB) have already been described in the prior art as major two-photon absorbing cage compounds. Historically, nitrobenzyl derived cages were developed first and were used under UV (1PA) photolysis conditions, typically in the λ=300-400 nm window, for the liberation of carboxylic acids, amides, phosphates, alcohols and carbonyl functions in particular, and were also used for the photorelease of proton (photoacid) and of metal ions. These derivatives have however the drawback of showing poor performances under 2PA conditions. The efficiency (Φ) of the fragmentation was improved either by the replacement of the benzyl function by a homobenzyl (Specht et al., ChemBioChem, 2006, 7, 1690-1695), or by the substitution of the benzylic position by an electron withdrawing group (EWG) such as ester or tri-bromomethyl groups. The most generally used nitrophenyl cages, such as α-carboxy-ortho-nitrobenzyl (CNB), ortho-nitrophenylethyl (NPE) and dimetoxy-ortho-nitrobenzyl derived compounds (DMNB), all having a two-photon cross-section $\delta_u$<0.1 GM at 720-980 nm wavelength, respond to the following formulas (Kuzyk et al., S. Characterization Techniques and Tabulations for Organic Nonlinear Optical Materials, 1998, Chapter 7; Kantevari et al., ChemBioChem, 2006, 7, 174-180; Kiskin et al., Eur. Biophys, J., 2002, 30, 588-604; Denk, Proc. Natl. Acad. Sci., 1994, 91, 6629-6633; Furuta et al., Proc. Natl. Acad. Sci., 1999, 96, 1193-1200):

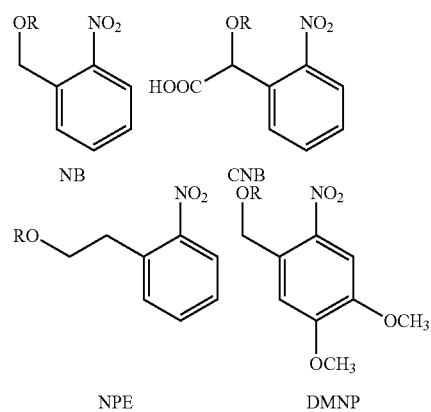

The poor 2PA absorption of the nitrophenyl derivatives sets a serious limitation of these caged compounds under 2PA conditions in biological experiments, unless using high peak power irradiation that may cause cellular damage.

The 7-nitroindoline derivative has also been described as a photoremovable protecting group (Amit et al., J. Am. Chem. Soc., 1976, 98, 843-844). The structure and the photochemical proprieties of this compound were considerably enhanced, particularly for photolysis in aqueous solution enabling their use in physiological experiments (Papageorgiou et al., J. Am., Chem. Soc., 1999, 121, 6503-6504; Papageorgiou et al., Tetrahedron, 2000, 56, 8197-8205). However, the nitroindoline caged amino acids present a weak two-photon cross-section, measured as 0.06 GM for 7-nitroindolinyl-glutamate, and show no hydrolysis at physiological pH.

Another class of caged compounds derives from 6-bromo-7-hydroxycoumarin-4-ylmethyl (BHC) derivatives, like the following compounds:

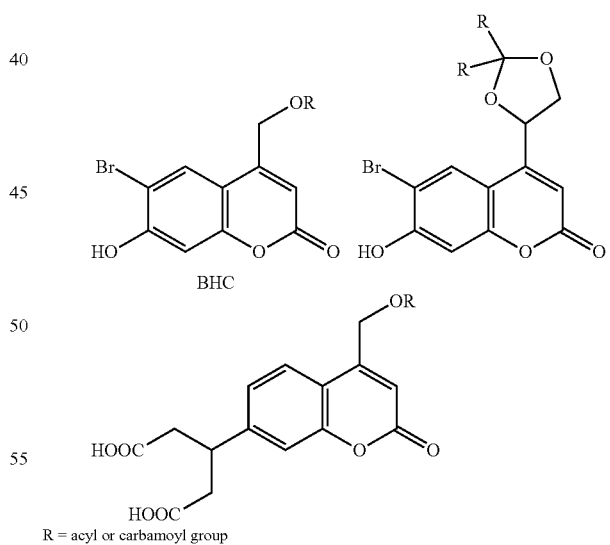

The photolysis of BHC derivatives can be easily followed by monitoring the variation of fluorescence due to the released coumarin, which is more intense than that of the starting compound. Di- or tri-halogenated coumarin derivatives lead to reasonably good 2PA uncaging cross-section but with less clean fragmentation reaction. Besides, the bromine substituent of the BHC derivatives may lower the phenol pKa, promoting the formation of a more strongly absorbing anion, and also decreasing the lipophilicity of the compound. As the coumarin photoproduct is highly fluorescent, it is an advantage in the following of the photolysis reaction, but also a limitation for the use of these cages in conjunction with fluorescent indicators. Moreover, BHC derivatives have low water solubility, which makes their use difficult under physiological conditions.

Thus, while there are reports in the prior art of approaches to the problem based on a wide range of different photolabile protecting groups, overall these have met with limited success. Indeed, the line and variety of multiphoton cage compounds are long, but many of these compounds have limited scopes, and a modest two-photon uncaging efficiency. Although considerable efforts have been made to develop systems activable by infrared (IR) light, the limitations of the photoactivable conjugates disclosed in the state of the art arise from the inefficient two-photon cross-sections reached, the difficulty of achieving high aqueous solubility of the coupled compounds, and the fact that irradiation may require wavelengths outside the range of the commercially available lasers.

Hence, there remains the need of providing photoactivable compounds having greatly improved photochemical, chemical and physiochemical properties for use with two-photon excitation by pulsed infrared (IR) radiation, compared to reagents currently available, and also showing an excellent solubility in physiological medium, and allowing high spatial and temporal control.

From the viewpoint of electronic structures and photophysical processes, there is a strong correlation between intramolecular charge-transfer processes and two-photon absorptivity. Thus, it follows that the permanent ground-state dipole moment as well as the transition dipole connected to either the ground state or the excited state are theoretically considered to be key factors in 2PA process. From the standpoint of designing an ideal molecular structure for a highly active 2PA chromophore, a number of key molecular features have been identified. With an intramolecular charge-transfer process as the driving force, the presence of an electron-rich (electron-donor) component, an electron-demanding (electron-acceptor) component, or both components is necessary, but not sufficient. In addition, the extent of conjugation has been identified as particularly important to the 2PA cross-section, as it leads to states with extended charge separation. Coplanarity is also critical in enhancing the efficiency of an intramolecular charge transfer.

Additionally, the ground-state dipole strength in non-symmetric molecules or the multipolar transition-dipole strength in centrosymmetric molecules has also been shown to greatly influence the 2PA in organic systems. Increasing the number of conjugation paths, or connecting several linear paths to form a two-dimensional (2D) or a three-dimensional (3D) configuration has also been shown theoretically and experimentally to be able to greatly increase 2PA responses.

The important benefit of multidimensional conjugation was recognized, and the use of molecular branching to further enhance the cross-section values of 2PA molecules was also demonstrated. This refined design concept led to a growing collection of multibranched 2PA organic compounds with the added dimensionality. Thus, two or more dipolar molecules are joined together with extended conjugation. The flow of intramolecular charge transfer can be either from the ends to the center of the molecule or vice versa ("outside in" or "inside out"). These types of 2PA chromophores are octupolar when their overall molecular geometry belongs to the following symmetry classification: (octahedral) Oh, (tetrahedral) Td, trigonal planar Dnh (n), and trigonal bipyramid (C3h).

Ideally, this design concept has two key elements that can result in a "cooperative effect" to enhance two-photon absorptivity:
   an increase in the number density of active 2PA units per molecule, and
   the synergistic interactions between the 2PA units via conjugation (through bonds) or perhaps "through-space but close-proximity" electronic interactions.

This concept can be applied successfully in the rational design of octupolar multiphoton activable D-A or D-π-A organic compounds responding to one of the following general structure:

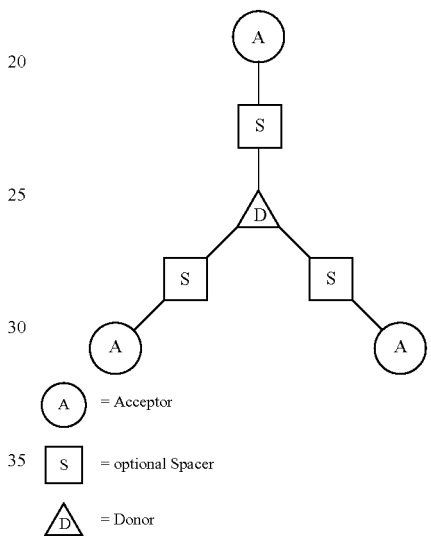

The inventors have now identified competitive novel compounds having $C_3$ symmetric tris-heteroarylamine donor-acceptor (D-A) or donor-π-acceptor (D-π-A) cores, structured around quinolines, as their primary structure.

The invention overcomes the inadequacies and disadvantages of the caged compounds disclosed in the prior the art by providing photoactivable compounds having greatly improved photochemical, chemical and physiochemical properties for use with two-photon excitation by pulsed infrared radiation (IR). More specifically, the compounds of the invention allow an external control of biological processes by light in accordance to noninvasive methodology which produced minimal perturbations of the cellular processes, and with the possibility of spatial and temporal control of drugs activation under in vivo conditions. The compounds of the invention allow the releasing of ligands ("small molecules") acting on intracellular receptors, under conventional light sources, and more particularly under infrared (IR) light in the window ranging from 720-800 nm, said compound presenting higher photorelease sensitivity under 2PA conditions. The two-photon excitation of the compounds of the invention is thus possible using mode-locked Ti:Sapphire lasers. The compounds of the invention are stable to hydrolysis, they are also water soluble and they present an improved solubility in physiological medium. Even more, as three "small molecules" can be released from the caged compound of the invention, the real concentration of the uncaged "small molecule" is three times higher in the final solution. The ability to link the substrate to the cage represents also a great flexibility that may allow the use of virtually all type of substrates having carboxy or phosphate linking groups. Another advantage in that the caged compounds of the invention can be easily stored (as their salts are crystalline solids), and that they are incomparably more stable at room temperature and even at daylight than the free bases. The photofragmentation also occurs very quickly after the irradiation in the dark, enabling the use of these compounds for the study of very fast events, such as the investigation of fast synaptic transmissions. Besides, their by-products are nontoxic.

A first subject of the present invention is therefore a novel compound responding to the following formula (I):

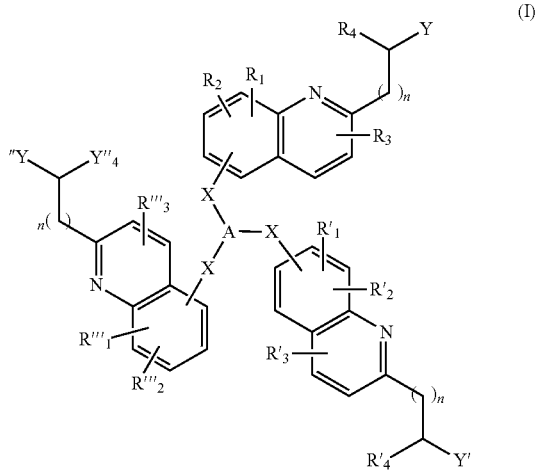

wherein:
n=0 or 1,
A represents a carbon, a nitrogen, a phosphorus or an arsenic atom,
X, which is an internal spacer, represents: a direct single bond between A and the quinoline group; an alkyne group —C≡C—; an alkene group —(R)C═C(R')—, in which R and R', identical or different, represent a hydrogen atom, an optionally substituted linear or branched alkyl or alkoxy group containing 1 to 30 carbon atoms, and preferably 1 to 6 carbon atoms; an optionally substituted aryl or heteroaryl group containing 5 to 18 atoms; an optionally substituted aralkyl, aralkylene or aralkyne group containing 6 to 18 atoms,
$R_1$, $R'_1$, $R''_1$, $R_2$, $R'_2$, $R''_2$, $R_3$, $R'_3$, $R''_3$, $R_4$, $R'_4$ and $R''_4$, identical or different, represent hydrogen or halogen atoms, amine, nitrile or nitro groups, optionally substituted linear or branched alkyl or alkoxy groups containing 1 to 30 carbon atoms, and preferably 1 to 6 carbon atoms, and
Y, Y' and Y", identical or different, represent halogen atoms, hydroxyl, azide, carboxylate —O(O)CR''', carbonate —O(O)COR''', carbamate —O(O)CNR''', phosphate —OP(O)(OR''')(OR'''') or phosphonate —OP(O)(OR''')(OR'''') groups, in which R''' and R'''', identical or different, represent hydrogen atoms, linear or branched alkyl groups containing 1 to 30 carbon atoms, and preferably 1 to 6 carbon atoms, optionally substituted by one or more groups independently selected from amino, amido, carboxy, hydroxyl, nitrile or nitro groups, and preferably amino and carboxy groups, and optionally comprising one or more ether, ester, amino, amido bridges.

According to a preferred embodiment of the present invention, A is a nitrogen atom.

In the sense of the present invention, the alkyl groups are preferably chosen among methyl, ethyl, n-propyl, isopropyl, n-butyl, tert-butyl and isobutyl radicals, and the alkoxy groups are preferably chosen among methoxy, ethoxy, ethyleneoxy, n-propyloxy, iso-propyloxy, n-butyloxy, tert-butyloxy and isobutyloxy radicals.

As used herein, the term "halogen" refers to a halogen atom selected from —F, —Cl, —Br and —I, and preferably from —Cl and —Br.

According to the invention, the term aralkyl refers to a radical derived from an alkyl radical in which a hydrogen atom is replaced by an aryl group, the term aralkenyl refers to a radical derived from an alkene radical in which a carbon of the double bond is directly linked to an aryl group, the term aralkenyl refers to a radical derived from an alkyne radical in which a carbon of the triple bond is directly linked to an aryl group.

In a preferred embodiment, X is a direct single bond between A and the quinoline group, an alkyne group —C≡C—, or a

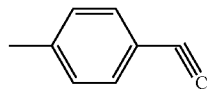

group.

According to the invention, aryl and heteroaryl groups refer to any functional group or substitutent derived from at least one simple aromatic ring; an aromatic ring corresponding to any planar cyclic compound having a delocalized π system in which each atom of the ring comprises a p-orbital, said p-orbitals overlapping themselves. Among aryl or heteroaryl groups, optionally substituted, one can mention phenyl, furan, pyridine, pyrrole, thiophene, imidazole, pyrazole, oxazole, isoxazole, thiazole, benzene, pyridine, pyrazine, pyrimidine, pyridazine, benzylcyclobutene, pentalene, benzofurane, isobenzofurane, indole, isoindole, benzothiophene, benzo[c]thiophene, benzimidazole, indazole, benzoxazole, benzisoxazole, benzothiazole, naphthalene, quinoline, isoquinoline, quinoxaline, quinazoline, cinnoline, purine, anthracene or acridine, the preferred aryl groups being substituted or non-substituted benzene.

According to another preferred alternative, Y, Y' and Y" are chosen among the following groups: —OH, —$N_3$, —Br, —Cl, —OC(O)$CH_3$, —OC(O)$CH_2CH_2$CH($NH_2$)COOH, —OC(O)CH($NH_2$)$CH_2CH_2$COOH, —OC(O)$NH_2$, —OC(O)$CH_2CH_2CH_2NH_2$.

The invention also relates to a general compound according to the invention responding to one of the following formula:

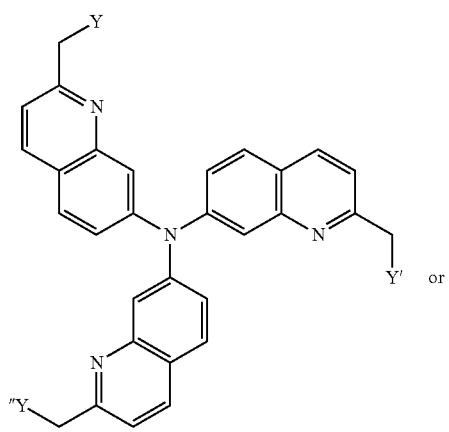
(II)
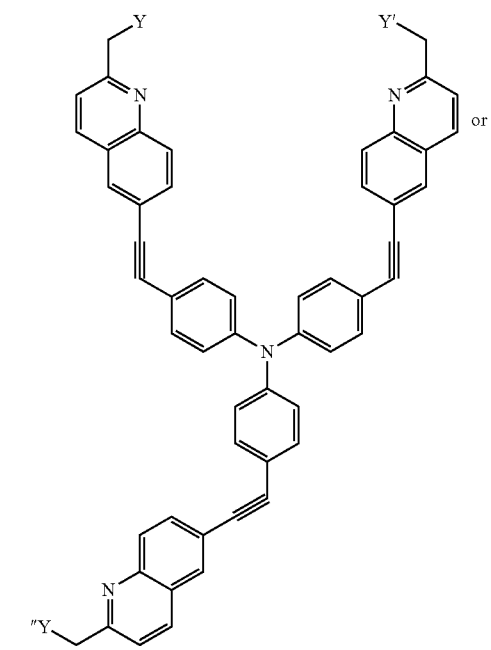
(IV)
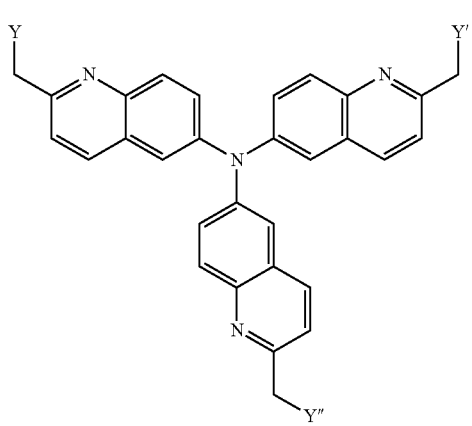
(III)
wherein Y, Y' and Y" have the same meaning as defined above.
The invention also relates to a general compound according to the invention responding to one of the following formula:
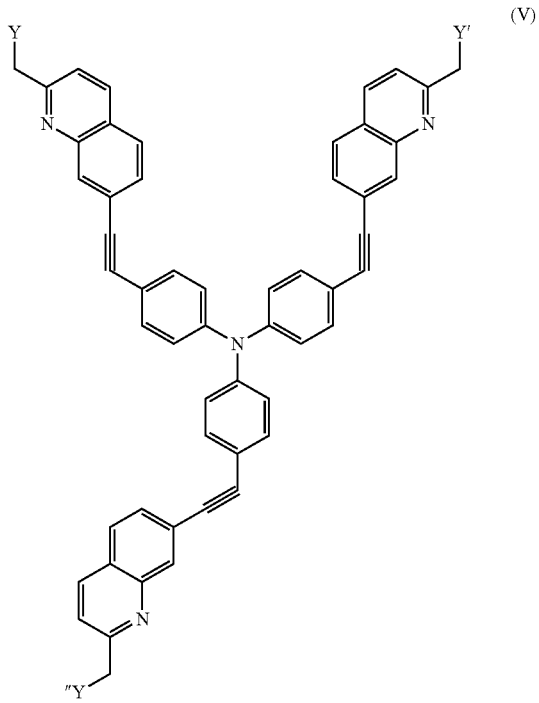
(V)
wherein Y, Y' and Y" have the same meaning as defined above.
The present invention also concerns the following specific compounds of formula (I):

11
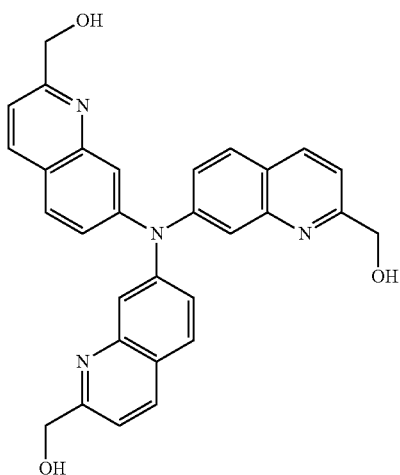
12
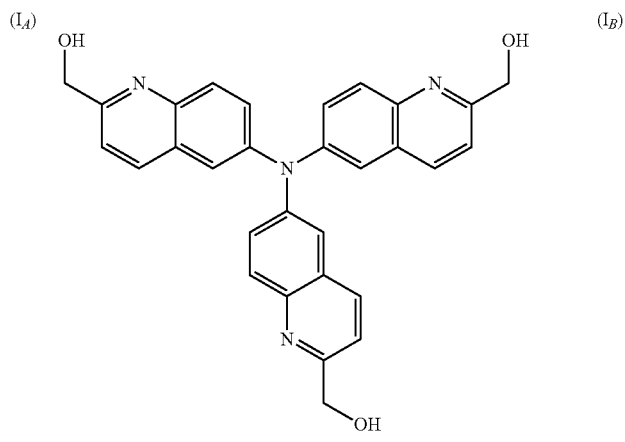
(I_A)
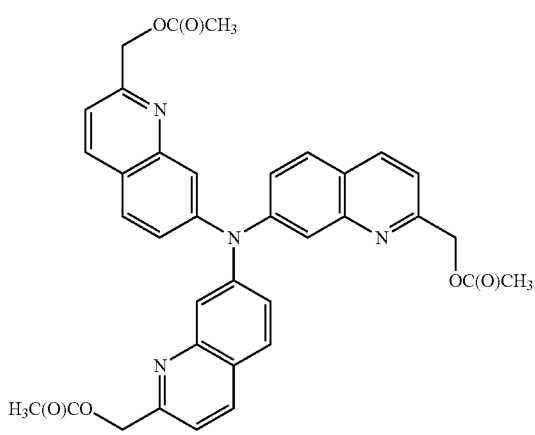
(I_C)
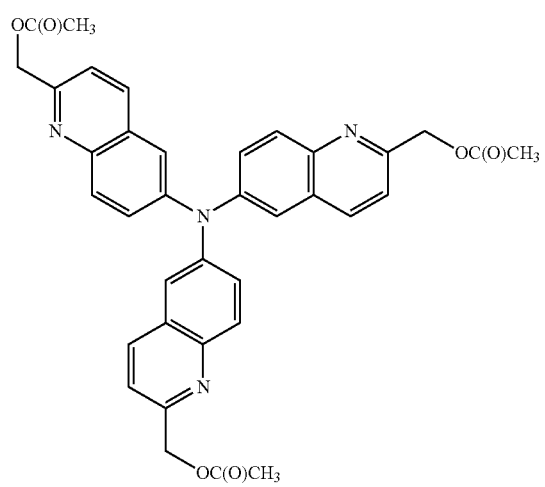
(I_D)
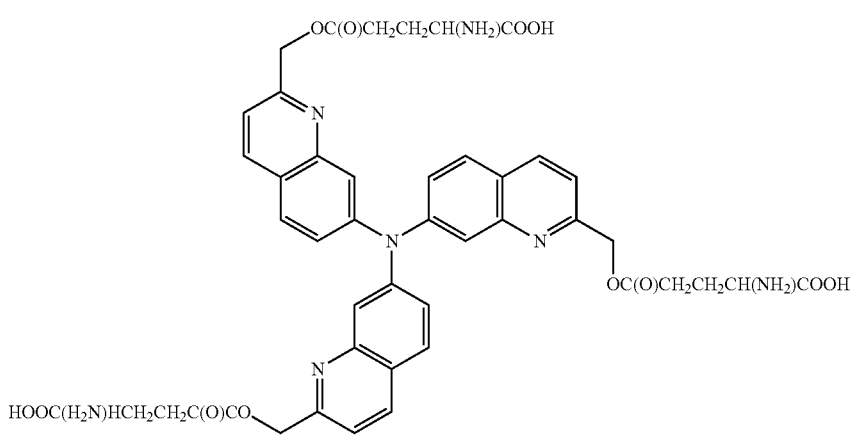
(I_E)

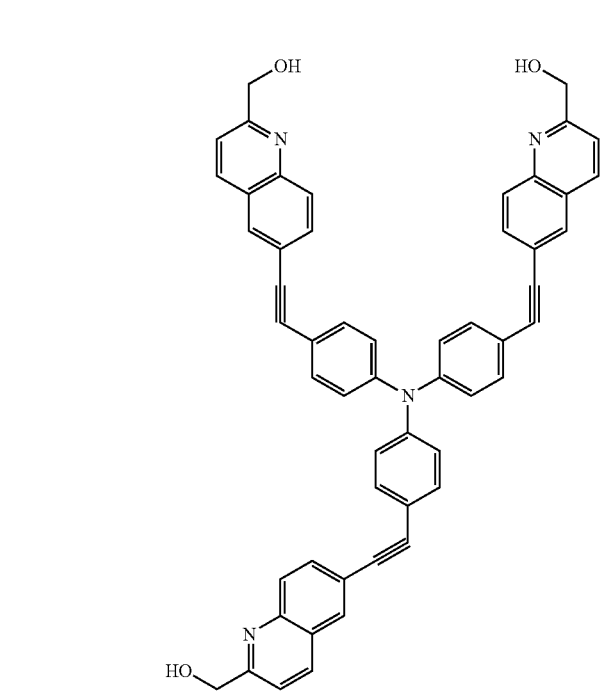

(I_F)

The second object of the invention relates to a specific method of synthesizing a compound according to the invention.

Said method comprises the following steps:

(i) a transformation step of an optionally substituted bromoaniline in a bromoquinaldine, preferably according to the Doebner-Miller reaction conditions described in Vogel's Textbook of Practical Organic Chemistry, Fifth Edition, Longman Scientific Technical, 1989, p. 1187, which is incorporated herewith by reference, (ii) an amination step of the bromine obtained in step (i), in the presence of copper and L-proline, such as described in Huang et al., J. Comb. Chem., 2008, 10, 617-619, which is incorporated herewith by reference, (iii) a reaction between the aminoquinaldine obtained in step (ii) and two equivalents of bromoquinaldine, preferably according to the Buchwald-Hartwig reaction conditions described in B. P. Fors et al. J. Am. Chem. Soc., 2009, 131, 5766-5768, and G. D. Vo, J. Am. Chem. Soc., 2009, 131, 11049-11061, which is incorporated herewith by reference, (iv) an oxidation step using preferably selenium dioxide, followed by a reduction step using preferably sodium borohydride.

According to a first alternative, the method of synthesis octupolar compounds such as (I_A) or (I_B) may comprise the following steps:

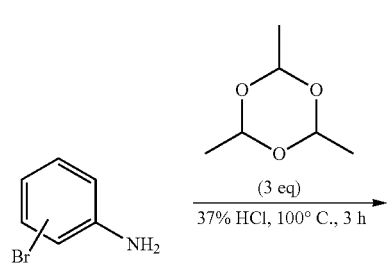

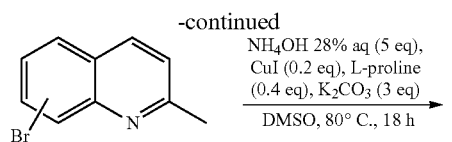

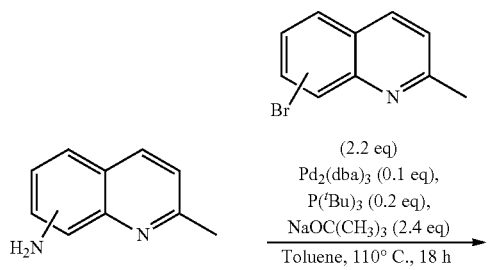

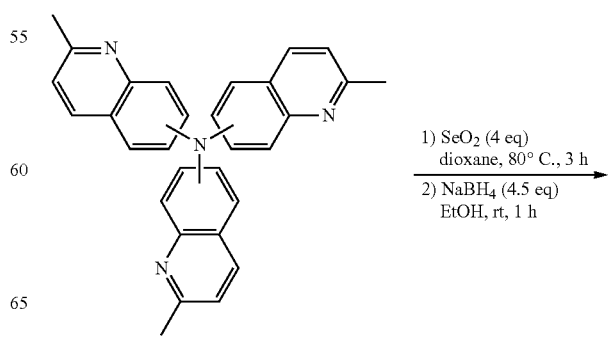

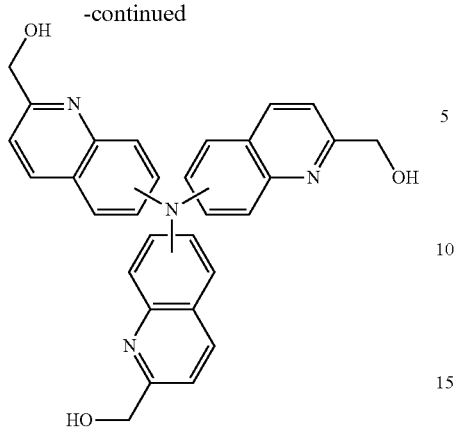
According to a second alternative, the method of synthesis octupolar compounds such as (I$_A$) or (I$_B$) may comprise the following steps:
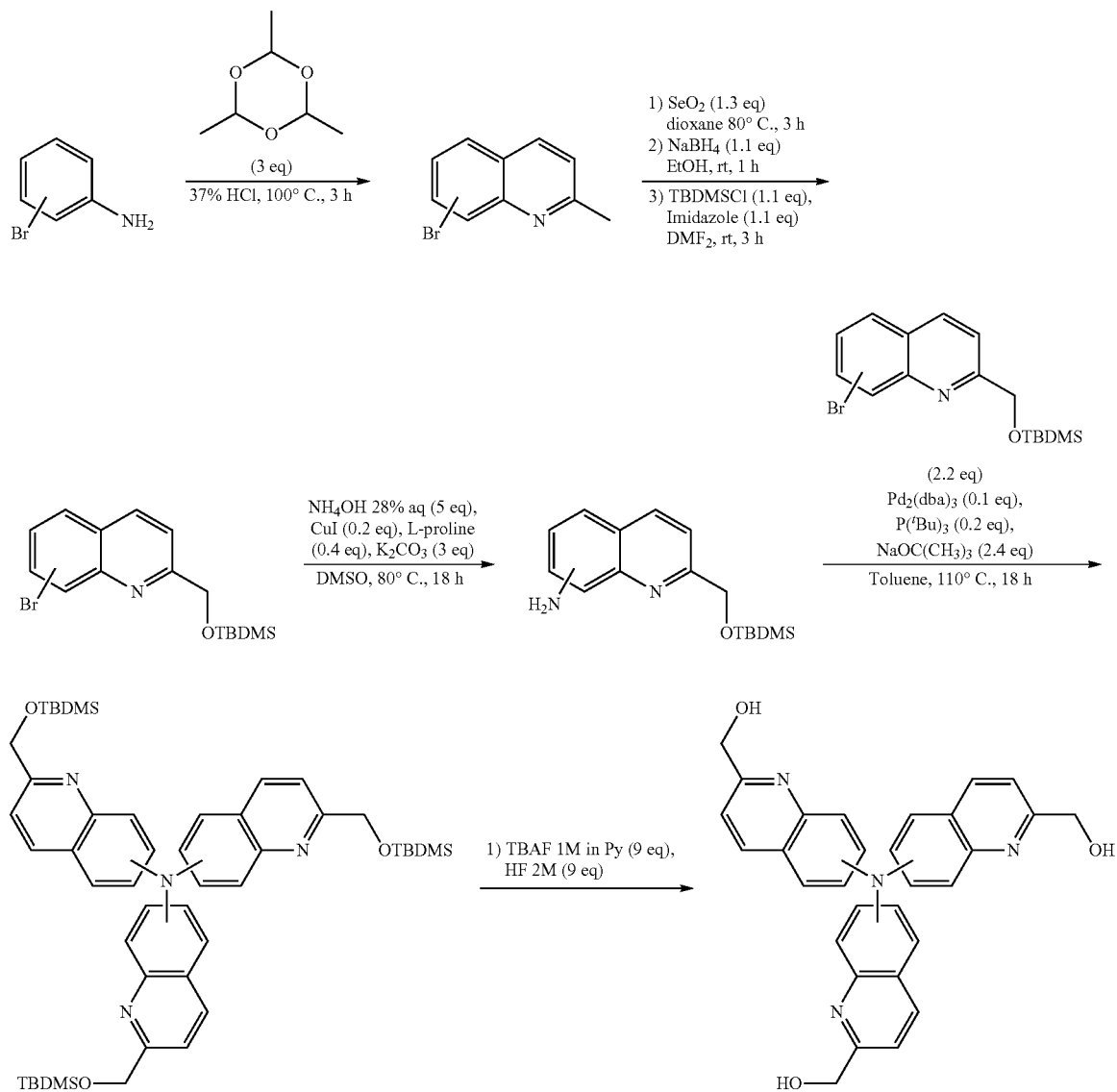

The key step of this synthesis is the iterative Sonogashira coupling (Huang et al. J. Org. Chem., 2008, 73, 6037-6040), which allows the efficient three-directional preparation of the triol end-product. The bromoquinaldines are transformed to the corresponding ethynyle-derivatives under Sonogashira conditions, by using TMS-acetylene, and then, after the deprotection of the TMS function, the alkyne-quinaldine is attached to the triarylamine via a second Sonogashira reaction. The isolation of the pure triol is obtained thanks to a selenium dioxide (SeO$_2$) oxidation, followed by sodium borohydride (NaBH$_4$) reduction.

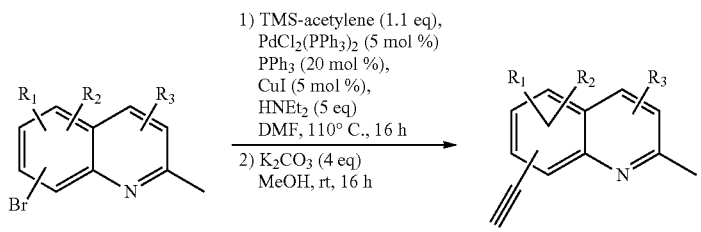

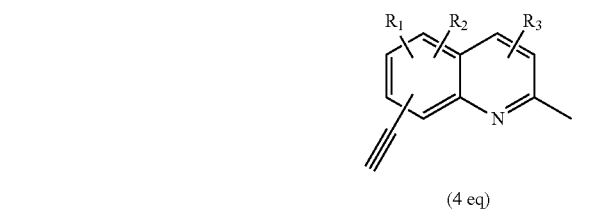

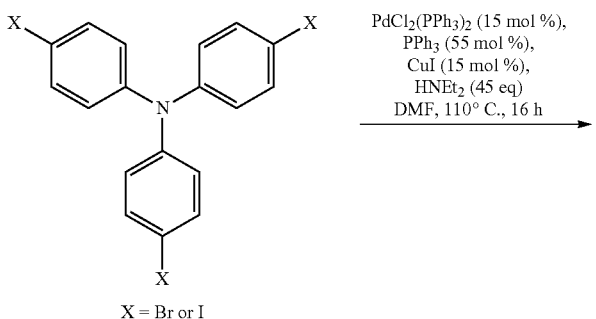

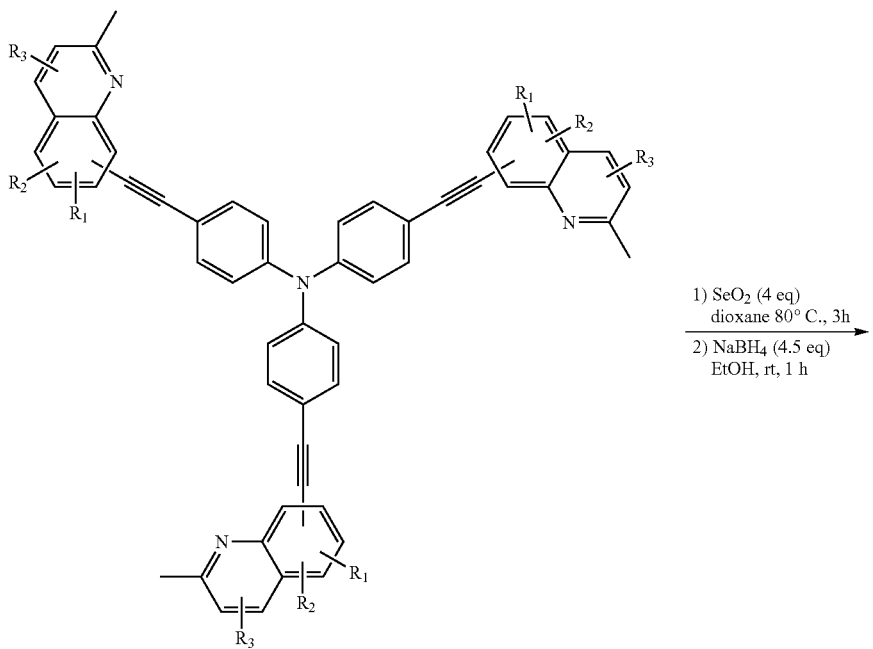

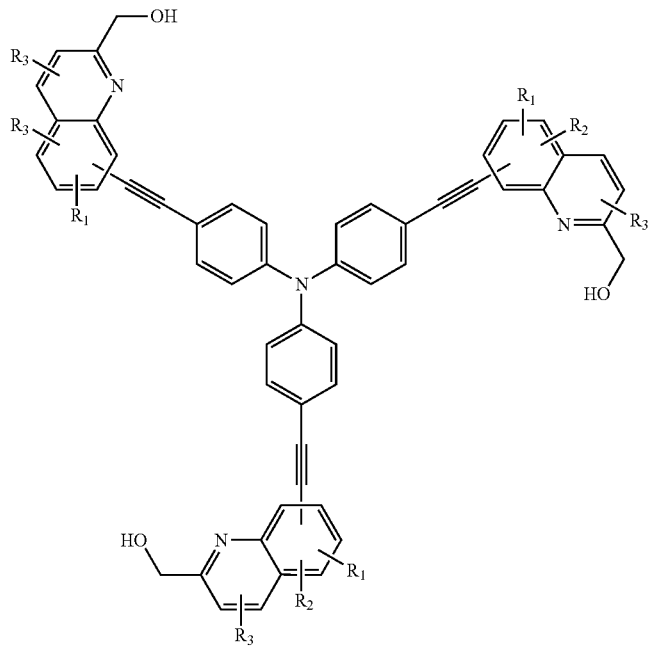

The alkyne group can be selectively transformed in alkene group by using catalytic hydrogenation with Lindlar catalyst; in dibromo alkene group by using excess of NBS (N-bromo succinimide) in chloroforme; in diene group by using tetra-cyanoethylene, as defined here-below (the group in dotted line being the group which can be modified):

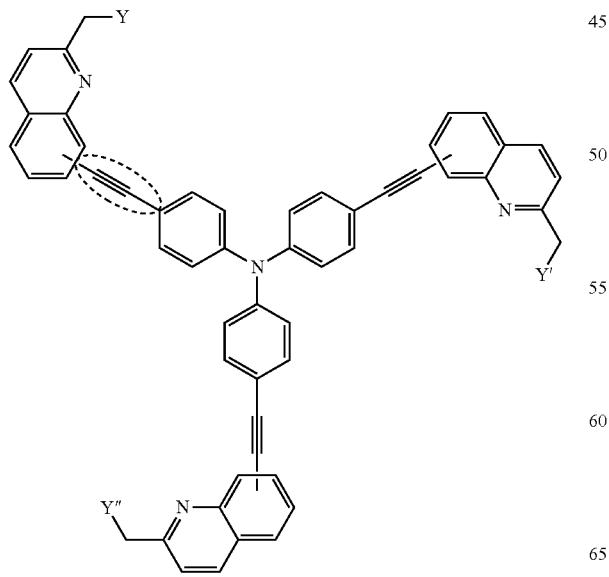

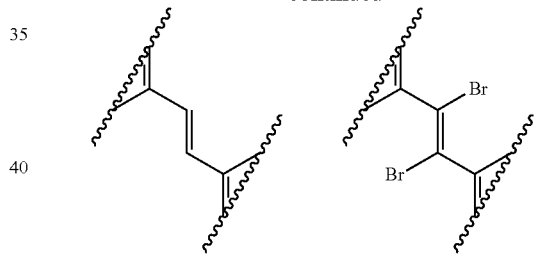

-continued

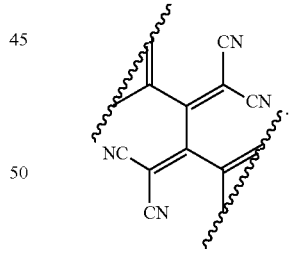

The caged substrates, named Y—H, Y'—H and/or Y"—H compounds when they are liberated, like acetate or glutamate substrates, can be prepared according different methods. Acetate substrates are prepared by using acetic anhydrides in the presence of dimethylaminopyridine (DMAP) and triethylamine in dichloromethane. The triglutamate substrates are prepared by using standard peptide-coupling conditions of N-Boc-glutamate-t-butyl ester including activation of the free acid by using dicyclohexylcarbodiimide (DCC), followed by the addition of the triol in the presence of triethylamine. The protecting groups can be cleaved in the presence of a strong acid, like trifluoroacetic acid.

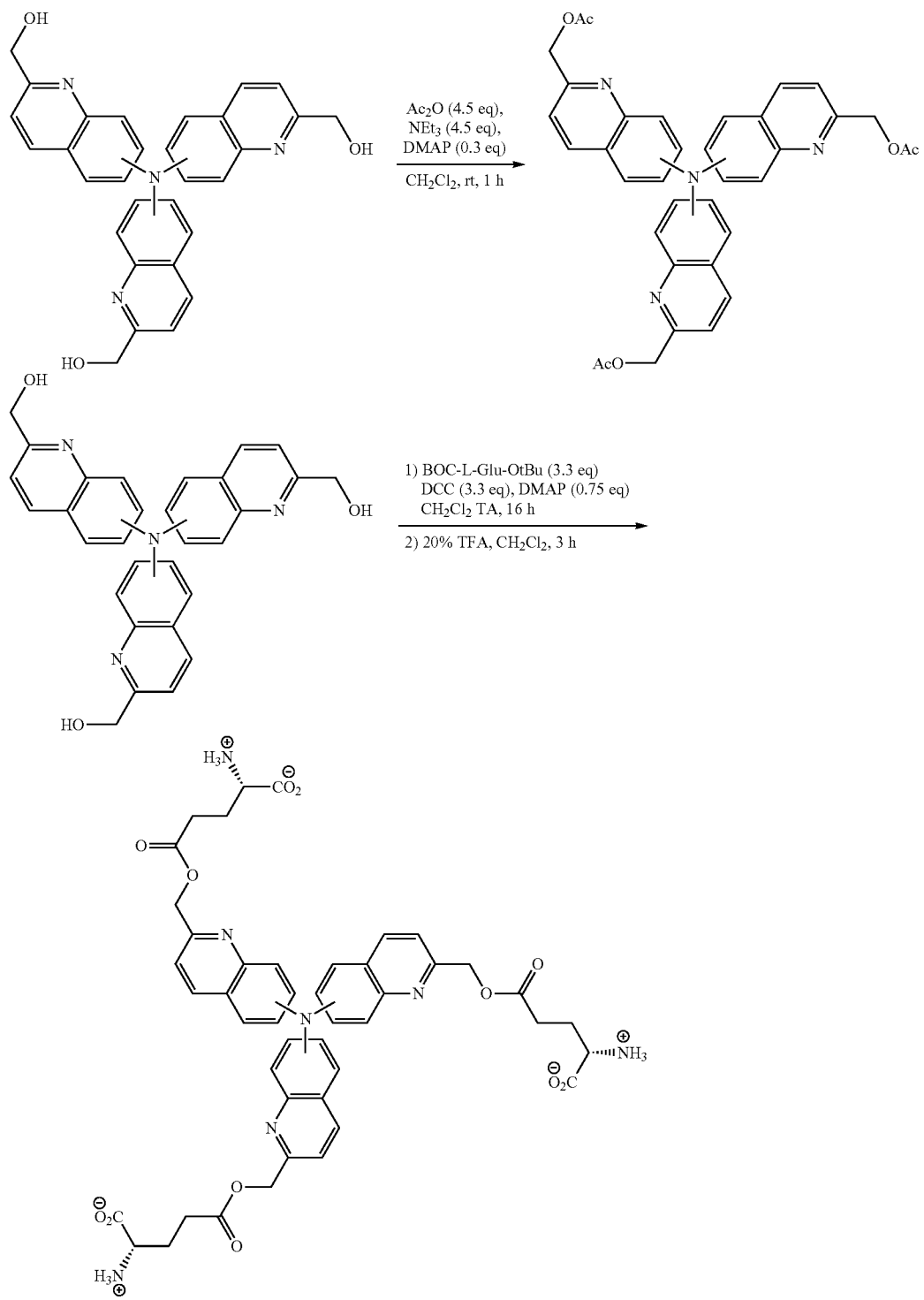

Then, the prepared compounds can be stored as HCl salts, and then they can be prepared by treatment of the compounds by HCl in dioxane, followed by a crystallization.

Another subject of the invention is an aqueous solution comprising at least one compound according to the invention, and more particularly three compounds according to the invention.

Preferably, the compound of the invention is present in said aqueous solution at a concentration ranging from $10^{-5}$ to $10^{-1}$ mol·L$^{-1}$.

According another embodiment, said aqueous solution has a pH of 6 to 8.

An additional subject of the invention is a method of liberating a Y—H, a Y'—H and/or a Y"—H compounds, said method comprising the step of irradiating a compound according to the invention, and thus releasing the Y—H, Y'—H and/or Y"—H compounds.

The mechanism of liberating a Y—H, a Y'—H and/or a Y"—H compounds can be summarized according to the following reaction:

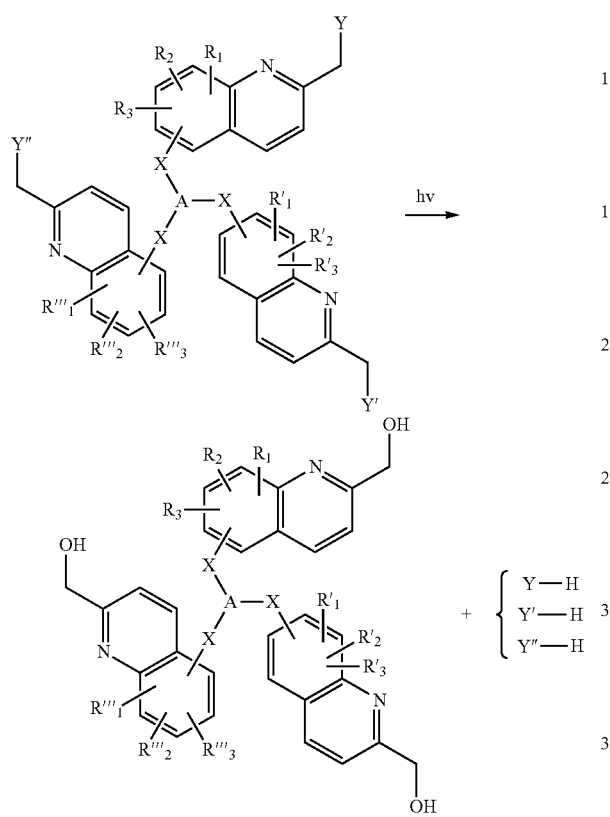

The irradiating step of the method of liberating a Y—H, a Y'—H and/or a Y"—H compounds is preferably carried out at a wavelength ranging from 600 to 1000 nm, and more preferably at a wavelength ranging from 650 to 800 nm. The photofragmentation is a stepwise process, which means that the liberation of one, then two, and then three substrates can be observed. The temperature of irradiation may vary from 0° C. to 60° C., and preferably the irradiation step is conducted at room temperature (19° C.), or at physiological temperature. The irradiation time depends on the laser power used and the type of experience, and may vary from the ms (millisecond) to 10 hours.

A final subject of the invention concerns a compound of the invention or an aqueous solution of the invention for use in a large scale of applications, like biological and medical fields, for the vectorisation or drug delivery of biologically and/or physiologically active substances of therapeutic interest of formula Y—H, Y'—H and/or Y"—H, for example into the intercellular space, or more particularly directly in the cells or tissues. In this case, the compounds or the aqueous solutions of the invention are injected into the intercellular space, or directly in the cells or tissues of a patient, and then submitted to an irradiating step, as defined above, thus liberating the Y—H, Y'—H and/or Y"—H compounds.

The compounds of the invention can also be used for the microfabrication of three dimensional (3D) microstructures chosen among microchannels, micropumps, cantilevers, plasmonic devices, and photonic crystals.

The modular assembly of these heterocycles gives a particular flexibility of the compounds. This approach enables facile access to a variety of relevant structures for the physicochemical tests. As a consequence, the compounds of the invention can be armed by a variety of substrates either of biological interest or relevant for the microfabrication of nano-materials.

In addition to the above provisions, the invention also comprises other provisions which will become clear from the description which follows, which refers to examples illustrating the advantages of the compounds of the invention, and also to the attached FIG. 1, which shows a simplified Jablonski diagram of the "simultaneous" two-photon absorption, and the observed fluorescence difference by 380 nm and 760 nm irradiation using 200 femto-seconds (fs) laser sources of a fluoresceine solution.

EXAMPLES

The proof of principle of the multiphoton activation was demonstrated for the compounds of the invention by preparing and testing acetate and glutamate analogues.

Example of Synthesis of Direct Attached Tris-Heteroarylamine Cage Compounds

The centrosymmetric octupolar cages of the invention were realized according to the following Scheme 1:

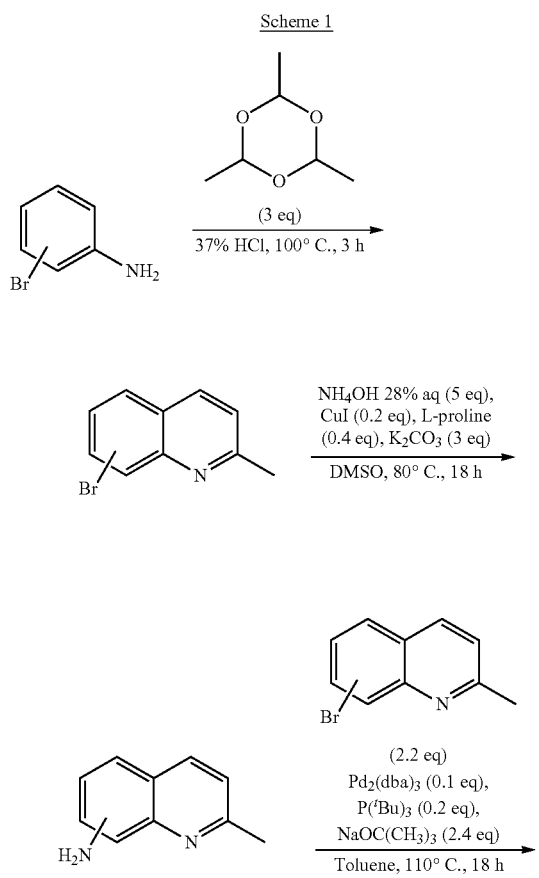

-continued

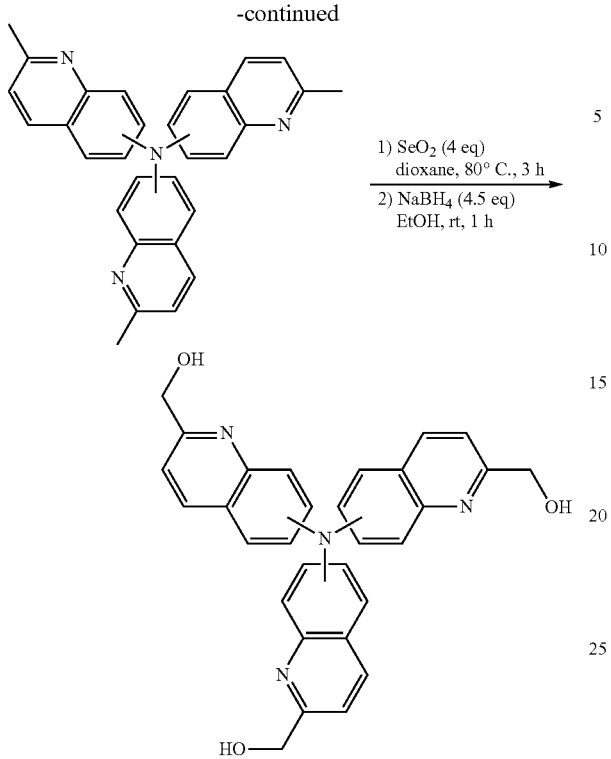

The synthesis of the octupolar cages, like ($I_A$) and ($I_B$), can be realized according two distinct chemical paths. As depicted in Scheme 1, the conveniently substituted starting bromoaniline is transformed in bromoquinaldine, using Doebner-Miller-type reaction conditions (Vogel's Textbook of Practical Organic Chemistry; Fifth Edition, Longman Scientific Technical, 1989, p. 1187). The bromine is replaced by —$NH_2$ in a copper-mediated amination, in the presence of L-proline as ligand. Then, the trimeric structure was assembled by using Buchwald-Hartwig amination conditions, with the aminoquinaldine and two equivalents of bromoquinaldine. In the final steps benzylic oxidation by using selenium dioxide, followed by a reduction with sodium borohydride, conducted to the isolation of the triol.

According to another sequence, the bromoquinaldine is transformed in a protected hydroxymethylene by a $SeO_2$-mediated benzylic oxidation and a reduction of the formed aldehyde by sodium borohydride in methanol, followed by the protection of the primary alcohol as a TBS (t-butyl dimethylsilylether). The amination of the bromoquinaldine using aqueous ammonia, followed by Buchwald-Hartwig amination and the deprotection of the TBS group by HF-pyridine, conducted to a pure triol.

Scheme 2

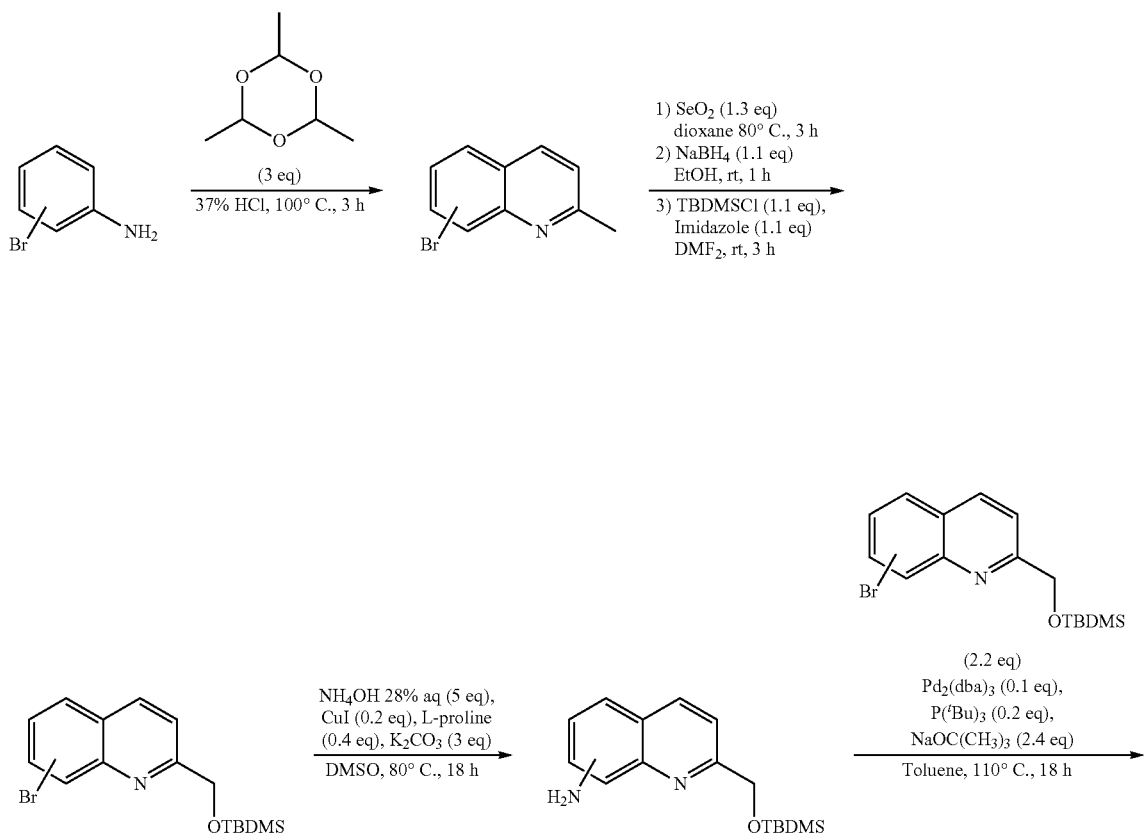

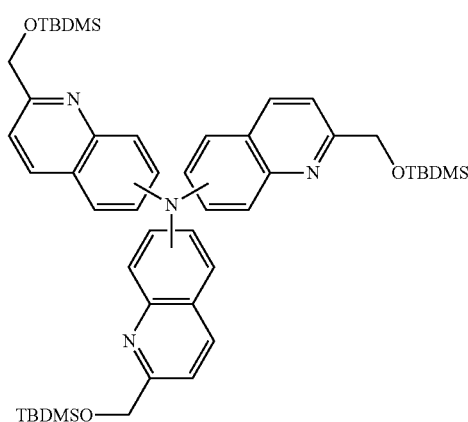 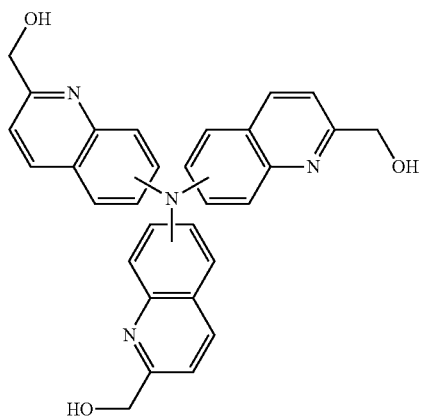

Example of Synthesis of Tris-Heteroarylamine Compounds Having an Internal Spacer The preparation of centrosymmetric cages having internal spacers consists of the transformation of the bromoquinaldines in the corresponding ethynyle-derivatives under Sonogashira conditions (by using TMS-acetylene), and then, after the deprotection of the TMS function, the alkyne-quinaldine (3 equivalents) is attached to the triarylamine with the help of a second Sonogashira reaction. The end of the sequence reiterates the same functional transformation steps as previously, and a $SeO_2$ oxidation followed by $NaBH_4$ reduction is conducted, allowing the isolation of the pure triol.

Scheme 3

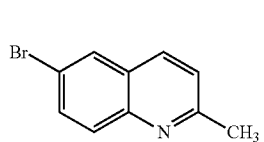
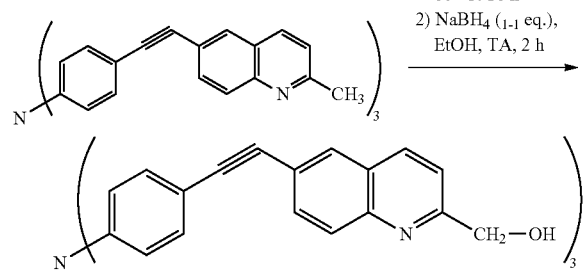

Preparation of Different Compounds According to the Invention

A—Preparation of {6-[tris-(2-hydroxymethyl-quinolin-6-yl)-amino]-quinolin-2-yl}-methanol 1) Preparation of 6-bromo-2-methyl-quinoline

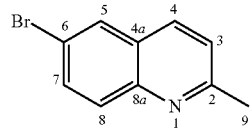

Doebner-Miller Synthesis:

4-bromoaniline (12.4 g, 55.6 mmol) was added to a solution of 37% HCl at 0° C. (24 mL). Paraldehyde (21 mL, 168 mmol, 3 eq) was then introduced and the mixture was left to react at room temperature for 1 hour, and then refluxed for 3 hours. After cooling to 0° C., sodium hydroxide (25 mL) was added dropwise, and the mixture was extracted with dichloromethane. The organic layer was washed twice with water and brine, then dried over $MgSO_4$, and concentrated under reduced pressure. The product was purified by column chromatography ($SiO_2$, Cyclohexane-AcOEt 9/1) and a white powder is obtained (5.9 g, 48%).

Molecular formula: $C_{10}H_8BrN$

Molecular weight: 222.08 g·mol$^{-1}$ $^1$H NMR: δ 7.92 (d, J=9.7 Hz, 1H, H$_8$), 7.87 (m, 2H, H$_4$, H$_5$), 7.71 (dd, J=9.7 Hz, J=2.0 Hz, 1H, H$_7$), 7.27 (d, J=9.7 Hz, 1H, H$_3$), 2.70 (s, 3H, CH$_{3(9)}$).

$^{13}$C NMR: δ 159.9 (s, $C_2$), 146.8 (s, $C_{8a}$), 135.6 (s, $C_4$), 133.2 (s, $C_7$), 130.7 (s, $C_8$), 129.9 (s, $C_5$), 128.0 (s, $H_{4a}$), 123.2 (s, $C_3$), 119.8 (s, $C_6$), 25.7 (s, $CH_{3(9)}$).

2) Preparation of 6-bromo-quinoline-2-carbaldehyde

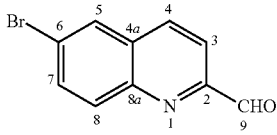

Selenium dioxyde (1.3 g, 12 mmol, 1.3 eq) in suspension in dioxane (50 mL) was heated at 60° C. 6-bromoquinaldine (2 g, 9 mmol) was then introduced and the mixture was left to react at 80° C. for 3 hours. After cooling to room temperature, the mixture was filtered on celite, eluted with dioxane and concentrated under reduced pressure. The product obtained is a pure white solid (3.3 g, >98%).

Molecular formula: $C_{10}H_6BrNO$

Molecular weight: 236.06 g·mol$^{-1}$ $^1$NMR: δ 10.17 (s, 1H, CHO), 8.19 (d, J=8.5 Hz, 1H, $H_4$), 8.08 (d, J=9.0 Hz, 1H; $H_8$), 8.04 (d, J=2.0 Hz, 1H, $H_5$), 8.02 (d, J=8.5 Hz, 1H, $H_3$).

ESI m/z: 236 (M+H$^+$), 268 (hemiacetal), 282 (acetal).

Rf=0.71 (Cyclohexane/EtOAc:3/1).

3) Preparation of (6-bromo-2-yl)-methanol

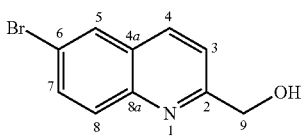

6-bromoquinoline-2-carbaldehyde (177 mg, 0.75 mmol) was added to EtOH (5 mL) at 0° C. Sodium borohydride (28.4 mg, 0.75 mmol, 1 eq) was then introduced and the mixture was stirred at room temperature for 1 hour. Ethanol was evaporated and water was added. The solution was extracted with dichloromethane and the organic layer was washed twice with water and brine, dried over MgSO$_4$, and concentrated under reduced pressure. Primary alcohol was obtained as a white powder (179 mg, >98%).

Molecular formula: $C_{10}H_8BrNO$

Molecular weight: 238.08 g·mol$^{-1}$ $^1$NMR: δ 8.06 (d, J=8.5 Hz, 1H, $H_4$), 7.95 (m, 2H, $H_5$ et $H_8$), 7.79 (d, J=8.7 Hz, 1H, $H_7$), 7.35 (d, J=8.5 Hz, 1H, $H_3$), 4.93 (s, 2H, $H_9$), 4.15 (b, 1H, OH).

$^{13}$C NMR: δ 160.8 (s, $C_2$), 148.5 (s, $C_{8a}$), 136.4 (s, $C_4$), 133.7 (s, $C_7$), 130.6 (s, $C_8$), 130.1 (s, $C_5$), 120.6 (s, $C_{4a}$), 119.7 (s, $C_6$), 64.5 (s, $C_9$).

MS (ESI): m/z=238.0, 240.0 [M+H]$^+$.

HRMS (ESI): m/z calculated for [$C_{10}H_8BrNO+H$]$^+$ 237.9868, found 237.9872 (ppm 1.9), 239.9847, found 239.9852 (ppm 2.1).

4) Preparation of 6-bromo-2-(tert-butyl-dimethyl-silanyloxymethyl)-quinoline

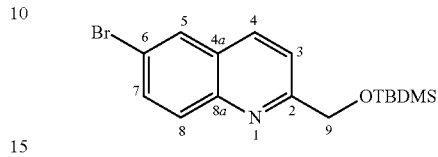

Primary alcohol (2 g, 8 mmol, 1 eq), TBDMSCl (1.4 g, 9 mmol, 1.1 eq) and imidazole (623 mg, 9 mmol, 1.1 eq) were added to DMF (20 mL). The resulting solution was stirred at room temperature for 3 hours, and then the solvent was removed under high reduced pressure. Cyclohexane was added and the mixture was washed twice with water, and then with brine. The organic layer was then dried over MgSO$_4$, and concentrated under reduced pressure. The product was obtained pure as a white solid (2.8 g, >98%).

Molecular formula: $C_{16}H_{22}BrNOSi$

Molecular weight: 352.34 g·mol$^{-1}$ $^1$NMR: δ 7.98 (d, J=8.5 Hz, 1H, $H_4$), 7.84 (s, 1H, $H_5$), 7.82 (d, J=8.5 Hz, 1H, $H_8$), 7.67 (d, J=8.5 Hz, 2H, $H_3$ et $H_7$), 4.95 (s, 2H, $H_9$), 0.95 (s, 9H, $^t$Bu), 0.95 (s, 6H, diMe).

$^{13}$C NMR: δ 162.6 (s, $C_2$), 146.2 (s, $C_{8a}$), 135.9 (s, $C_4$), 133.2 (s, $C_7$), 130.8 (s, $C_8$), 130.0 (s, $C_5$), 128.8 (s, $H_{4a}$), 120.0 (s, $C_6$), 119.6 (s, $C_3$), 67.0 (s, $C_9$), 26.3 (s, $^t$Bu), 18.7 (s, $^t$Bu), −4.8 (s, diMe).

R$_f$=0.48 (Cyclohexane/EtOAc:3/1).

MS (ESI): m/z=351.9, 353.9 [M+H]$^+$.

HRMS (ESI): m/z calculated for [$C_{16}H_{22}BrNOSi+H$]$^+$ 352.0732, found 352.0743 (ppm 3.0), 354.0712, found 354.0726 (ppm 4.0).

5) Preparation of 2-(tert-butyl-dimethyl-silanyloxymethyl)-quinoline-6-ylamine

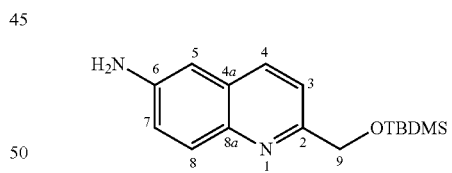

The protected bromoquinoline derivative (600 mg, 1.7 mmol, 1 eq), copper iodide (65 mg, 0.3 mmol, 20 mol %), L-proline (78 mg, 0.7 mmol, 40 mol %) and K$_2$CO$_3$ (705 mg, 5 mmol, 3 eq) were dissolved in DMSO (20 mL). Aqueous ammonia NH$_4$OH at 28% (1.6 mL) was then introduced and the mixture was heated at 80° C. for 18 hours. After cooling to room temperature, dichloromethane was added followed by a saturated NH$_4$Cl solution. The aqueous layer was extracted twice with dichloromethane, and the combined organic layers were washed again with a saturated NH$_4$Cl solution. The product was purified by column chromatography (SiO$_2$, Cyclohexane-AcOEt 1/1) and obtained as a white powder (300 mg, 61%).

Molecular formula: $C_{16}H_{24}N_2OSi$

Molecular weight: 288.46 g·mol$^{-1}$

¹H NMR (250 MHz): δ 7.90 (d, J=8.5 Hz, 1H, H$_8$), 7.83 (d, J=8.7 Hz, 1H, H$_4$), 7.57 (d, J=8.5 Hz, 1H, H$_7$), 7.11 (d, J=8.7 Hz, 1H, H$_3$), 6.86 (s, 1H, H$_5$), 4.96 (s, 2H, H$_9$), 3.98 (s, 2H, NH$_2$), 0.97 (s, 9H, $^t$Bu), 0.13 (s, 6H, di Me).

¹³C NMR (250 MHz): δ 158.2 (s, C$_2$), 144.7 (s, C$_6$), 142.6 (s, C$_{8a}$), 134.9 (s, C$_4$), 130.1 (s, C$_8$), 129.2 (s, C$_{4a}$), 122.0 (s, C$_3$), 119.3 (s, C$_7$), 108.0 (s, C$_5$), 67.1 (s, C$_9$), 26.4 (s, $^t$Bu), 18.8 (s, $^t$Bu), −4.8 (s, diMe).

ESI m/z: 289.1 (M+H$^+$).

R$_f$=0.16 (Cyclohexane/EtOAc: 3/1).

MS (ESI): m/z=289.2 [M+H]$^+$.

HRMS (ESI): m/z calcd for [C$_{16}$H$_{24}$N$_2$OSi+H]$^+$ 289.1736, found 289.1732 (ppm −1.4).

6) Preparation of tris-[2-(tert-butyl-dimethyl-silanyloxymethyl)-quinoline-6-yl]-amine In a sealed tube placed in the glove box, the amino derivative (100 mg, 0.3 mmol, 1 eq), the bromo derivative (269 mg, 0.8 mmol, 2.2 eq), dipalladium tris-dibenzylideneacetone (Pd$_2$dba$_3$) (70 mg, 0.07 mmol, 20 mol %) and sodium tertbutoxide NaOC(CH$_3$)$_3$ (73 mg, 0.8 mmol, 2.2 eq) were introduced. 1 M solution of tritertbutylphosphine P$^t$Bu$_3$ (64 μL, 0.3 mmol, 80 mol %) and distilled toluene (1.7 mL) were added and the tube was sealed. The mixture was heated at 110° C. for 18 hours. After cooling to room temperature, cyclohexane was added and the organic layer was washed twice with water and brine. The product was purified by column chromatography (SiO$_2$, Cyclohexane-AcOEt 9/1) and obtained as a yellow powder (268 mg, 95%).

Molecular formula: C$_{48}$H$_{66}$N$_4$O$_3$Si$_3$

Molecular weight: 831.32 g·mol$^{-1}$

¹H NMR: δ 7.97 (m, 2H, H$_4$ et H$_8$), 7.66 (d, J=8.7 Hz, 1H, H$_7$), 7.62 (d, J=8.5 Hz, 1H, H$_3$), 7.49 (s, 1H, H$_5$), 5.02 (s, 2H, H$_9$), 1.00 (s, 9H, $^t$Bu), 0.17 (s, 6H, di Me).

¹³C NMR: δ 161.2 (s, C$_2$), 145.4 (s, C$_6$), 144.9 (s, C$_{8a}$), 136.1 (s, C$_4$), 130.5 (s, C$_8$), 128.8 (s, C$_{4a}$), 128.3 (s, C$_3$), 120.7 (s, C$_7$), 119.4 (s, C$_5$), 67.1 (s, C$_9$), 26.4 (s, $^t$Bu), 18.8 (s, $^t$Bu), −4.8 (s, diMe).

ESI m/z: 831.3 (M+H$^+$).

R$_f$=0.12 (Cyclohexane/EtOAc:9/1), 0.68 (Cyclohexane/EtOAc: 2/1).

¹H NMR (250 MHz): δ 7.97 (m, 2H, H$_4$H$_8$), 7.66 (d, J=8.7 Hz, 1H, H$_7$), 7.62 (d, J=8.5 Hz, 1H, H$_3$), 7.49 (s, 1H, H$_5$), 5.02 (s, 2H, H$_9$), 1.00 (s, 9H, $^t$Bu), 0.17 (s, 6H, diMe).

¹³C NMR (63 MHz): δ 161.2 (s, C$_2$), 145.4 (s, C$_6$), 144.9 (s, C$_{8a}$), 136.1 (s, C$_4$), 130.5 (s, C$_8$), 128.8 (s, C$_{4a}$), 128.3 (s, C$_3$), 120.7 (s, C$_7$), 119.4 (s, C$_5$), 67.1 (s, C$_9$), 26.4 (s, $^t$Bu), 18.8 (s, $^t$Bu), −4.8 (s, diMe).

MS (ESI): m/z=831.3 [M+H]$^+$.

HRMS (ESI): m/z calculated for [C$_{48}$H$_{66}$N$_4$O$_3$Si$_3$+H]$^+$ 831.4521, found 831.4560 (ppm 4.7).

7) Preparation of tris-(2-methyl-quinolin-6-yl)-amine

In a sealed tube placed in the glove box, the 6-aminoquinoline derivative (400 mg, 2.5 mmol, 1 eq), the 6-bromoquinoline derivative (1.2 g, 5.4 mmol, 2.2 eq), Pd$_2$ dba$_3$ (259 mg, 0.25 mmol, 10 mol %) and sodium tertbutoxide NaOC(CH$_3$)$_3$ (577 mg, 6.0 mmol, 2.4 eq) were introduced. 1 M in toluene solution of tri-tertbutylphosphine P$^t$Bu$_3$ (106 μL, 0.5 mmol, 20 mol %) and distilled toluene (12 mL) were added and the tube was sealed. The mixture was heated at 110° C. for 18 hours. After cooling to room temperature, the solvent was removed under reduced pressure, then dichloromethane was added and the organic layer was washed twice with water and brine. The product was purified by column chromatography (SiO$_2$, Dichloromethane-MeOH 99/1) and obtained as a yellow powder (781 mg, 71%).

Molecular formula: C$_{30}$H$_{24}$N$_4$

Molecular weight: 440.54 g·mol$^{-1}$

¹H NMR (250 MHz): δ 7.92 (d, J=8.7 Hz, 1H, H$_8$), 7.74 (d, J=8.3 Hz, 1H, H$_4$), 7.53 (d, J=8.7 Hz, 1H, H$_7$), 7.38 (s, 1H, H$_5$), 7.15 (d, J=8.3 Hz, 1H, H$_3$), 2.67 (s, 3H, H$_9$).

¹³C NMR (125 MHz): δ 158.1 (s, C$_2$), 145.4 (s, C$_6$), 145.1 (s, C$_{8a}$), 135.6 (s, C$_4$), 130.3 (s, C$_8$), 128.1 (s, C$_{4a}$), 127.8 (s, C$_3$), 122.8 (s, C$_7$), 120.5 (s, C$_5$), 25.5 (s, C$_9$).

ESI m/z: 441.3 (M+H$^+$).

8) Preparation of tris-(quinolin-6-yl-2-carbaldehyde)-amine

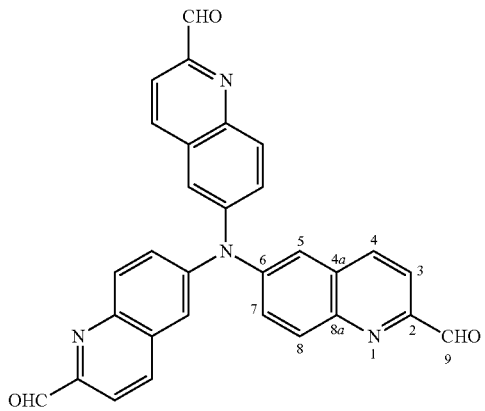 [SMILES: O=Cc1ccc2cc(N(c3ccc4nc(C=O)ccc4c3)c3ccc4nc(C=O)ccc4c3)ccc2n1]

Selenium dioxide (108 mg, 1.0 mmol, 3.3 eq) in suspension in dioxane (2 mL) was heated at 60° C. 6-tris-quinoline (100 mg, 0.3 mmol) was the introduced and the mixture was left to react at 80° C. for 3 hours. After cooling to room temperature, the mixture was filtered on celite, eluted with dioxane and concentrated under reduced pressure. The product was purified by column chromatography (SiO$_2$, Cyclohexane-AcOEt 4/1) and obtained as a yellow oil (43 mg, 30%).

Molecular formula: $C_{30}H_{18}N_4O_3$
Molecular weight: 482.49 g·mol$^{-1}$
$^1$H NMR (acetone d6, 250 MHz): δ 10.15 (s, 3H, CHO), 8.41 (d, J=8.5 Hz, 3H, H$_4$), 8.26 (d, J=8.5 Hz, 3H, H$_3$), 7.97 (d, J=8.5 Hz, 3H, H$_8$), 7.88 (m, 6H, H$_5$ and H$_7$).
$^{13}$C NMR (75 MHz): δ 194.4 (s, CHO), 153.5 (s, C$_2$), 148.4 (s, C$_6$), 146.9 (s, C$_{8a}$), 138.0 (s, C$_4$), 133.4 (s, C$_8$), 132.9 (s, C$_{4a}$), 130.2 (s, C$_7$), 122.4 (s, C$_3$), 119.0 (s, C$_5$).

9) Preparation of {6-[tris-(2-hydroxymethyl-quinolin-6-yl)-amino]quinolin-2-yl}-methanol

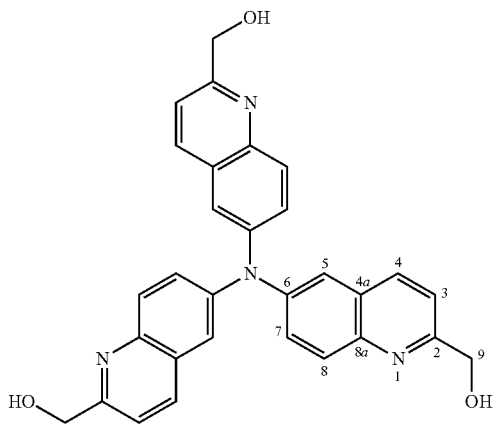 [SMILES: OCc1ccc2cc(N(c3ccc4nc(CO)ccc4c3)c3ccc4nc(CO)ccc4c3)ccc2n1]

6-tris-quinoline-2-carbaldehyde (50 mg, 0.1 mmol) was added to EtOH (0.5 mL) at 0° C. Sodium borohydride (18 mg, 0.47 mmol, 4.5 eq) was then introduced and the mixture was stirred at room temperature for 1 hour. Ethanol was evaporated and water was added. The solution was extracted with dichloromethane and the organic layer was washed twice with water and brine, dried over MgSO$_4$, and concentrated under reduced pressure. Tris-alcohol was obtained as a yellow oil (38 mg, 80%).

Molecular formula: $C_{30}H_{24}N_4O_3$
Molecular weight: 488.54 g·mol$^{-1}$
$^1$H NMR (500 MHz): δ 8.04 (d, J=9.0 Hz, 3H, H$_8$), 7.91 (d, J=8.0 Hz, 3H, H$_4$), 7.61 (dd, J=9.0 Hz, J=2.0 Hz, 3H, H$_7$), 7.61 (d, J=2.0 Hz, 3H, H$_5$), 7.25 (d, J=8.0 Hz, 3H, H$_3$), 4.90 (s, 6H, H$_9$).
ESI m/z: 489.2 (M+H$^+$).
R$_f$=0.11 (RP18, MeOH/H$_2$O: 3/2).
$^1$H NMR (500 MHz) (MeOD): δ 8.92 (bb, 3H, H$_7$), 8.48 (d, J=6.5 Hz, 3H, H$_4$), 8.10 (dd, J=8.0 Hz, J=3.0 Hz, 6H, H$_8$H$_3$), 8.05 (d, J=3.0 Hz, 3H, H$_5$), 5.23 (s, 6H, H$_9$), 4.86 (bb, 3H, OH).
$^{13}$C NMR (75 MHz) (MeOD): δ 161.3 (s, C$_2$), 148.0 (s, C$_6$), 146.8 (s, C$_{8a}$), 136.7 (s, C$_4$), 133.6 (s, C$_{4a}$), 131.2 (s, C$_7$), 123.9 (s, C$_8$), 123.5 (s, C$_5$), 121.7 (s, C$_3$), 62.0 (s, C$_9$).
MS (ESI): m/z=489.1 [M+H]$^+$.
HRMS (ESI): m/z calculated for [C$_{30}$H$_{24}$N$_4$O$_3$+H]$^+$ 489.1927, found 489.1916 (ppm 2.2).
HPLC-MS: (Method C): rt=16.57 min, m/z=489.1, extraction at 260 and 360 nm, λ$_{max}$=371 nm.

9) Preparation of acetic acid [6-(bis-(2-acetoxymethyl-quinolin-6-yl)-amino)-quinolin-2-yl]-methyl ester "6-tripode-OAc"

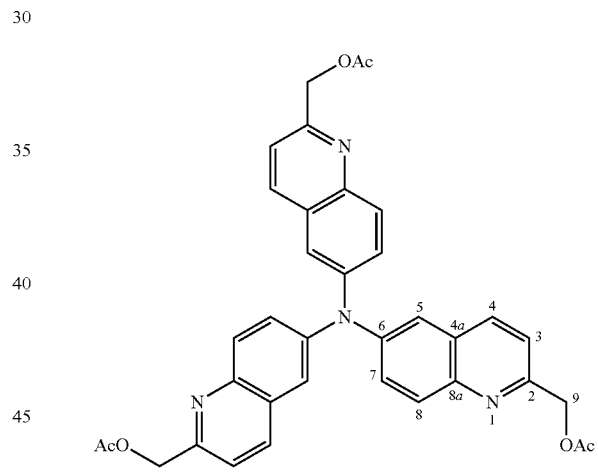

Tris alcohol 9 (11 mg, 0.02 mmol), triethylamine (14 μL, 0.1 mmol, 4.5 eq), acetic anhydride (10 μL, 0.1 mmol, 4.5 eq) and a catalytic amount of DMAP were dissolved in dichloromethane (100 μL) and the mixture was stirred at room temperature for 2 hours in the dark. The crude product was then purified by column chromatography on silica gel (Dichloromethane-MeOH 95:5) to afford compound triacetate as a yellow oil (11 mg, 89%).

Molecular formula: $C_{36}H_{30}N_4O_6$
Molecular weight: 614.65 g·mol$^{-1}$
R$_f$=0.21 (Cyclohexane/EtOAc: 1/3).
$^1$H NMR (500 MHz): δ 8.01 (d, J=9.0 Hz, 3H, H$_8$), 7.90 (d, J=8.5 Hz, 3H, H$_4$), 7.58 (dd, J=9.0 Hz, J=2.5 Hz, 3H, H$_7$), 7.43 (d, J=2.5 Hz, 3H, H$_5$), 7.39 (d, J=8.5 Hz, 3H, H$_3$), 5.34 (s, 6H, H$_9$), 2.15 (s, 9H, OAc).
$^{13}$C NMR (125 MHz): δ 172.0 (s, CO), 156.6 (s, C$_2$), 146.8 (s, C$_6$), 146.5 (s, C$_{8a}$), 137.3 (s, C$_4$), 132.1 (s, C$_7$), 130.0 (s, C$_{4a}$), 129.5 (s, C$_8$), 121.6 (s, C$_3$C$_5$), 68.8 (s, C$_9$), 22.3 (s, OAc).

MS (ESI): m/z=615.3 [M+H]$^+$.
HRMS (ESI): m/z calculated for [C$_{36}$H$_{30}$N$_4$O$_6$+H]$^+$ 615.2244, found 615.2233 (ppm −1.7).
UV (MeCN): $\lambda_{max}$=366 nm, $\epsilon(\lambda_{max})$=13900 M$^{-1}$·cm$^{-1}$.

B—Preparation of {7-[tris-(2-hydroxymethyl-quinolin-7-yl)-amino]quinolin-2-yl}-methanol 1) Preparation of 7-bromo-2-methyl-quinoline

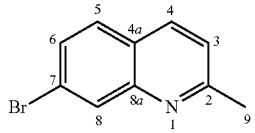

Doebner-Miller Synthesis:
3-bromoaniline (3 mL, 27 mmol), was added to a solution of 37% HCl at 0° C. (24 mL). Paraldehyde (8 mL, 83 mmol, 3 eq) was then introduced and the mixture was left to react at room temperature for 1 hour, then refluxed for 3 hours. After cooling to 0° C., sodium hydroxide (25 mL) was added dropwise and the mixture was extracted with dichloromethane. The organic layer was washed twice with water and brine, then dried over MgSO$_4$, and concentrated under reduced pressure. The product was purified by column chromatography (SiO$_2$, Cyclohexane-AcOEt 9/1) and obtained as a white solid (2.8 g, 46%).
Molecular formula: C$_{10}$H$_8$BrN
Molecular weight: 222.08 g·mol$^{-1}$
IR (film): 1610, 1494, 1264, 841, 736 cm$^{-1}$
Melting Point: 57° C.
$^1$H NMR: δ 8.09 (s, 1H, H$_8$), 7.80 (d, J=8.2 Hz, 1H, H$_4$), 7.39 (m, 2H, H$_5$ and H$_7$), 7.12 (d, J=8.2 Hz, 1H, H$_3$), 2.61 (s, 3H, H$_9$).
$^{13}$C NMR: δ 160.3 (s, C$_2$), 148.6 (s, C$_{8a}$), 136.2 (s, C$_4$), 131.2 (s, C$_8$), 129.4 (s, C$_5$), 128.9 (s, C$_6$), 125.3 (s, C$_{4a}$), 123.7 (s, C$_7$), 122.6 (s, C$_3$), 25.7 (s, C$_9$).
R$_f$=0.33 (Cyclohexane/EtOAc: 2/1), 0.73 (Cyclohexane/EtOAc:1/1).

2) Preparation of 7-bromo-quinoline-2-carbaldehyde

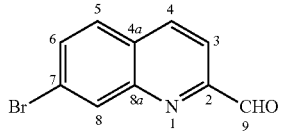

Selenium dioxide (1.6 g, 14 mmol, 1.3 eq) in suspension in dioxane (50 mL) was heated at 60° C. 7-bromoquinaldine (2.5 g, 11.2 mmol) was the introduced and the mixture was left to react at 80° C. for 3 hours. After cooling to room temperature, the mixture was filtered on celite, eluted with dioxane and concentrated under reduced pressure. The product was obtained pure as a white solid (3.3 g, >98%).
Molecular formula: C$_{10}$H$_6$BrNO
Molecular weight: 236.06 g·mol$^{-1}$
IR (film): 1701, 1587, 1298, 911, 843, 757 cm$^{-1}$
Melting point: 151° C.

SM-IC$^+$ (CH$_3$OH) m/z: 236 (M+H$^+$), 268 (hemiacetal), 282 (acetal).
MS (ESI): m/z=236.0, 238.0 [M+H]$^+$, 258.0, 260.0 [M+Na]$^+$, 268.0, 270.0 (hemiacetal), 282.0, 284.0 (acetal).
HRMS (ESI): m/z calculated for [C$_{10}$H$_6$BrNO+H]$^+$ 235.9711, found 235.9702 (ppm −3.8); 237.9691, found 237.9681 (ppm −4.0).

3) Preparation of (7-bromo-quinolin-2-yl)-methanol

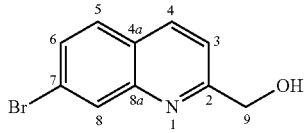

7-bromoquinoline-2-carbaldehyde (177 mg, 0.75 mmol) was added to EtOH (5 mL) at 0° C. Sodium borohydride (28.4 mg, 0.75 mmol, 1 eq) was then introduced and the mixture was stirred at room temperature for 1 hour. Ethanol was evaporated and water was added. The solution was extracted with dichloromethane and the organic layer was washed twice with water and brine, dried over MgSO$_4$, and concentrated under reduced pressure. Primary alcohol was obtained as a white powder (179 mg, >98%).
Molecular formula: C$_{10}$H$_8$BrNO
Molecular weight: 238.08 g·mol$^{-1}$
R$_f$=0.25 (Cyclohexane/EtOAc: 3/1).
$^1$H NMR (250 MHz): δ 8.19 (s, 1H, H$_8$), 8.06 (d, J=8.5 Hz, 1H, H$_4$), 7.64 (d, J=8.5 Hz, 1H, H$_6$), 7.57 (d, J=8.0 Hz, 1H, H$_5$), 7.32 (d, J=8.5 Hz, 1H, H$_3$), 4.91 (s, 2H, C$_9$), 4.60 (bb, 1H, OH).
$^{13}$C NMR (63 MHz): δ 160.9 (s, C$_2$), 147.5 (s, C$_{8a}$), 137.1 (s, C$_4$), 131.2 (s, C$_8$), 130.3 (s, C$_6$), 129.3 (s, C$_5$), 126.4 (s, C$_{4a}$), 124.3 (s, C$_7$), 119.2 (s, C$_3$), 64.6 (s, C$_9$).
MS (ESI): m/z=238.0; 240.0 [M+H]$^+$.
HRMS (ESI): m/z calculated for [C$_{10}$H$_8$BrNO+H]$^+$ 237.9868, found 237.9872 (ppm 1.9); 239.9847, found 239.9852 (ppm 2.1).

4) Preparation of 2-methyl-quinolin-7-ylamine

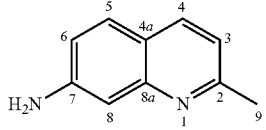

The 7-bromoquinoline derivative (800 mg, 3.6 mmol, 1 eq), copper iodide (137 mg, 0.7 mmol, 20 mol %), L-proline (166 mg, 1.4 mmol, 40 mol %) and K$_2$CO$_3$ (1.5 g, 11 mmol, 3 eq) were dissolved in DMSO (20 mL). Aqueous ammonia 28% NH$_4$OH (2 mL) was then introduced and the mixture was heated at 80° C. for 18 hours. After cooling to room temperature, dichloromethane was added followed by a saturated NH$_4$Cl solution. The aqueous layer was extracted twice with dichloromethane, and the combined organic layers were washed again with a saturated NH$_4$Cl solution. The product was purified by column chromatography (SiO$_2$, Cyclohexane-AcOEt 1/3) and obtained as a white powder (511 mg, 90%).

Molecular formula: $C_{10}H_{10}N_2$

Molecular weight: 158.20 g·mol$^{-1}$ $^1$H NMR (500 MHz): δ 7.69 (d, J=8.0 Hz, 1H, H$_4$), 7.38 (d, J=8.5 Hz, 1H, H$_5$), 7.04 (s, 1H, H$_8$), 7.85 (d, J=8.0 Hz, 1H, H$_3$), 6.77 (d, J=8.5 Hz, 1H, H$_6$), 4.26 (bb, 2H, NH$_2$), 2.58 (s, 3H, H$_9$).

$^{13}$C NMR (125 MHz): δ 160.3 (s, C$_2$), 151.0 (s, C$_{8a}$), 149.6 (s, C$_7$), 137.1 (s, C$_4$), 129.9 (s, C$_5$), 121.5 (s, C$_{4a}$), 119.6 (s, C$_4$), 119.0 (s, C$_6$), 109.8 (s, C$_8$), 42.2 (s, C$_9$).

R$_f$=0.20 (Dichloromethane/MeOH:95/5).

ESI m/z: 159.2 (M+H$^+$).

5) Preparation of tris-(2-methyl-quinolin-7-yl)-amine

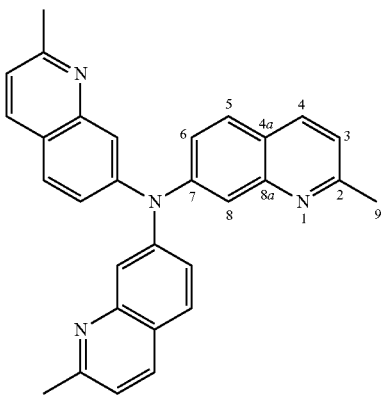 [SMILES: Cc1ccc2ccc(N(c3ccc4ccc(C)nc4c3)c3ccc4ccc(C)nc4c3)cc2n1]

In a sealed tube placed in the glove box, the 6-aminoquinoline derivative (400 mg, 2.5 mmol, 1 eq), the 6-bromoquinoline derivative (1.2 g, 5.4 mmol, 2.2 eq), Pd$_2$dba$_3$ (259 mg, 0.25 mmol, 10 mol %) and sodium tertbutoxide NaOC(CH$_3$)$_3$ (577 mg, 6.0 mmol, 2.4 eq) were introduced. 1 M in toluene solution of tritertbutylphosphine P$^t$Bu$_3$ (106 µL, 0.5 mmol, 20 mol %) and distilled toluene (12 mL) were added and the tube was sealed. The mixture was heated at 110° C. for 18 hours. After cooling to room temperature, the solvent was removed under reduced pressure, then dichloromethane was added and the organic layer was washed twice with water and brine. The product was purified by column chromatography (SiO$_2$, Dichloromethane-MeOH 99/1) and obtained as a yellow powder (715 mg, 65%).

Molecular formula: $C_{30}H_{24}N_4$

Molecular weight: 440.54 g·mol$^{-1}$ $^1$H NMR (250 MHz): δ 7.93 (d, J=8.3 Hz, 1H, H$_4$), 7.68 (d, J=8.5 Hz, 1H, H$_5$), 7.66 (d, J=2.5 Hz, 1H, H$_8$), 7.40 (dd, J=8.5 Hz, J=2.5 Hz, 1H, H$_6$), 7.15 (d, J=8.3 Hz, 1H, H$_3$), 2.63 (s, 3H, H$_9$).

$^{13}$C NMR (125 MHz): δ 159.8 (s, C$_2$), 149.4 (s, C$_{8a}$), 148.6 (s, C$_7$), 136.0 (s, C$_4$), 129.0 (s, C$_5$), 124.4 (s, C$_6$), 123.9 (s, C$_{4a}$), 122.5 (s, C$_3$), 121.2 (s, C$_8$), 25.6 (s, C$_9$).

R$_f$=0.36 (Dichloromethane/MeOH:95/5).

ESI m/z: 441 (M+H$^+$), 881 (2M+H$^+$).

6) Preparation of {7-[tris-(2-hydroxymethyl-quinolin-7-yl)-amino]-quinolin-2-yl}-methanol

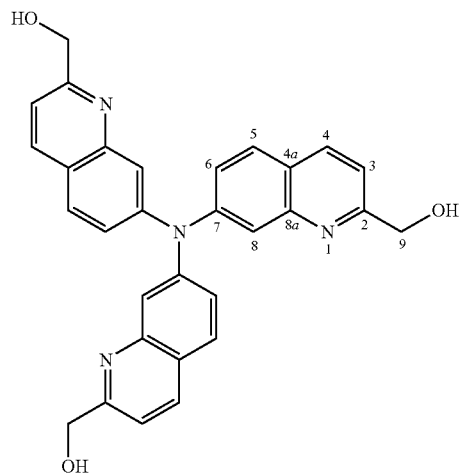 [SMILES: OCc1ccc2ccc(N(c3ccc4ccc(CO)nc4c3)c3ccc4ccc(CO)nc4c3)cc2n1]

First Synthesis:

Selenium dioxide (108 mg, 1.0 mmol, 3.3 eq) in suspension in dioxane (2 mL) was heated at 60° C. Tris-(2-methyl-quinolin-7-yl)-amine (100 mg, 0.3 mmol) was introduced and the mixture was left to react at 80° C. for 3 hours. After cooling to room temperature, the mixture was filtered on celite, eluted with dioxane and concentrated under reduced pressure. A part of the obtained trisaldehyde (60 mg, 0.12 mmol) was added to EtOH (0.5 mL) at 0° C. Sodium borohydride (16 mg, 0.42 mmol, 4.5 eq) was then introduced and the mixture was stirred at room temperature for 1 hour. Ethanol was evaporated and water was added. The solution was extracted with dichloromethane and the organic layer was washed twice with water and brine, dried over MgSO$_4$, and concentrated under reduced pressure. Triol was obtained as a yellow oil (20 mg, 8% over two steps).

Second Synthesis:

The tris-[2-(tert-butyl-dimethyl-silanyloxymethyl)-quinoline-6-yl]-amine (35 mg, 0.04 mmol, 1.0 eq) was dissolved in distilled THF. To the mixture was then added a solution of TBAF 1 M in THF (672 µL) and the medium was stirred at room temperature for 3 hours. After concentrated under reduced pressure, the crude product was transformed as a salt by adding HCl/ether. After removing the filtrate the salt was recrystallized from MeOH. An HCl salt as a yellow crystal was obtained (14 mg, 70%).

Molecular formula: $C_{30}H_{24}N_4O_3$

Molecular weight: 488.54 g·mol$^{-1}$

R$_f$=0.12 (RP18, MeOH/H$_2$O: 7/3).

$^1$H NMR (250 MHz) (CDCl$_3$): δ 8.07 (d, J=8.5 Hz, 1H, H$_4$), 7.76 (d, J=8.5 Hz, 1H, H$_5$), 7.75 (d, J=2.0 Hz, 1H, H$_8$), 7.45 (dd, J=8.5 Hz, J=2.0 Hz, 1H, H$_6$), 7.19 (d, J=8.5 Hz, 1H, H$_3$), 4.84 (s, 2H, H$_9$).

(D$_2$O) (salt): δ 9.06 (d, J=8.5 Hz, 3H, H$_6$), 8.36 (d, J=9.0 Hz, 3H, H$_4$), 8.19 (s, 3H, H$_8$), 7.97 (d, J=8.5 Hz, 3H, H$_5$), 7.91 (d, J=9.0 Hz, 3H, H$_3$), 5.27 (s, 6H, H$_9$).

$^{13}$C NMR (125 MHz) (CDCl$_3$): δ 160:1 (s, C$_2$), 148.6 (s, C$_{8a}$), 148.4 (s, C$_7$), 136.8 (s, C$_4$), 129.4 (s, C$_5$), 125.1 (s, C$_{4a}$), 125.0 (s, C$_3$), 122.3 (s, C$_6$), 117.8 (s, C$_8$), 64.5 (s, C$_9$).

(D$_2$O) (salt): δ 160.9 (s, C$_2$), 151.7 (s, C$_{8a}$), 148.0 (s, C$_7$), 140.3 (s, C$_4$), 132.9 (s, C$_5$), 128.6 (s, C$_6$), 127.6 (s, C$_{4a}$), 120.2 (s, C$_3$), 115.1 (s, C$_8$), 62.0 (s, C$_9$).

MS (ESI): m/z=489.2 [M+H]$^+$.

HPLC-MS: (Method C): rt=17.21 min, m/z=489.2 [M+H]$^+$, extraction at 260 and 360 nm, λ$_{max}$=386 nm.

Molecular formula: C$_{30}$H$_{24}$N$_4$O$_3$

Molecular weight: 488.54 g·mol$^{-1}$ $^1$H NMR (250 MHz): δ 8.07 (d, J=8.5 Hz, 1H, H$_4$), 7.76 (d, J=8.5 Hz, 1H, H$_5$), 7.75 (d, J=2.0 Hz, 1H, H$_8$), 7.45 (dd, J=8.5 Hz, J=2.0 Hz, 1H, H$_6$), 7.19 (d, J=8.5 Hz, 1H, H$_3$), 4.84 (s, 2H, H$_9$).

$^{13}$C NMR (125 MHz): δ 160.1 (s, C$_2$), 148.6 (s, C$_{8a}$), 148.4 (s, C$_7$), 136.8 (s, C$_4$), 129.4 (s, C$_5$), 125.1 (s, C$_{4a}$), 125.0 (s, C$_3$), 122.3 (s, C$_6$), 117.8 (s, C$_8$), 64.5 (s, C$_9$).

ESI m/z: 489.2 (M+H$^+$).

C—Preparation of an Ethynyl Centrosymmetric Cage According to the Invention

1) Preparation of 2-methyl-5-trimethylsilanylethynyl-quinoline

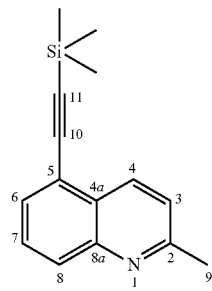 [SMILES: Cc1ccc2c(C#C[Si](C)(C)C)cccc2n1]

In a sealed tube were introduced 5-bromo-2-methyl-quinoline (1.0 g, 4.5 mmol, 1.0 eq), PdCl$_2$(PPh$_3$)$_3$ (154 mg, 0.22 mmol, 5% mol), copper iodide (42 mg, 0.22 mmol, 5% mol), and triphenylphosphine (236 mg, 0.9 mmol, 20% mol). Then, DMF (10 mL) was added followed by diethylamine (9.5 mL, 68 mmol, 15 eq) and trimethylsilylacetylene (700 µL, 5.0 mmol, 1.1 eq). The mixture was heated at 110° C. overnight. After cooling down the solvent was evaporated and the crude product was purified by column chromatography (Florisil, Cyclohexane-EtOAc 95:5) to afford 2-methyl-5-trimethylsilanylethynyl-quinoline as a white solid (970 mg, 90%).

Molecular formula: C$_{15}$H$_{17}$NSi

Molecular weight: 239.39 g·mol$^{-1}$

R$_f$=0.26 (Cyclohexane/EtOAc: 95/5).

$^1$H NMR: δ 8.45 (d, J=8.7 Hz, 1H, H$_8$), 7.97 (d, J=8.2 Hz, 1H, H$_4$), 7.60 (d, J=8.7 Hz, 1H, H$_7$), 7.55 (d, J=8.7 Hz, 1H, H$_6$), 7.28 (d, J=8.2 Hz, 1H, H$_3$), 2.69 (s, 3H, H$_9$), 0.33 (s, 9H, TMS).

$^{13}$C NMR: δ 159.7 (s, C$_2$), 147.8 (s, C$_{8a}$), 134.9 (s, C$_4$), 130.5 (s, C$_6$), 130.1 (s, C$_7$), 129.0 (s, C$_8$), 127.3 (s, C$_{4a}$), 123.0 (s, C$_3$), 121.1 (s, C$_5$), 102.3 (s, C$_{10}$), 100.3 (s, C$_{11}$), 25.6 (s, C$_9$), 0.49 (s, TMS).

2) Preparation of 5-ethynyl-2-methyl-quinoline

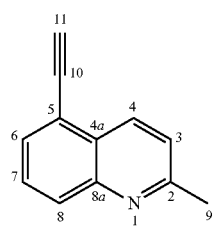

To a solution of 2-methyl-5-trimethylsilanylethynyl-quinoline (140 mg, 0.6 mmol, 1.0 eq) in solution in MeOH (5 mL) was added K$_2$CO$_3$ (324 mg, 2.34 mmol, 4 eq), and the resulting mixture was stirred overnight at room temperature. The solvent was then removed under reduced pressure and water was then added. The aqueous layer was extracted twice with cyclohexane, and then the combined organic layers were washed with brine and dried over MgSO$_4$. After filtration and concentration under reduced pressure the crude product was purified by column chromatography on silica gel (Cyclohexane-EtOAc 99:1) to afford 5-ethynyl-2-methyl-quinoline as a yellow oil (99 mg, 98%).

Molecular formula: C$_{12}$H$_9$N

Molecular weight: 167.21 g·mol$^{-1}$

R$_f$=0.30 (Cyclohexane/EtOAc:95/5).

$^1$H NMR (250 MHz): δ 8.50 (d, J=8.2 Hz, 1H, H$_8$), 8.03 (d, J=8.5 Hz, 1H, H$_4$), 7.71 (d, J=8.2 Hz, 1H, H$_7$), 7.61 (d, J=8.2 Hz, 1H, H$_6$), 7.35 (d, J=8.5 Hz, 1H, H$_3$), 347 (s, 1H, H$_{11}$), 2.75 (s, 3H, H$_9$).

$^{13}$C NMR (63 MHz): δ 160.0 (s, C$_2$), 147.8 (s, C$_{8a}$), 134.8 (s, C$_4$), 131.0 (s, C$_6$), 130.4 (s, C$_7$), 129.1 (s, C$_8$), 127.5 (s, C$_{4a}$), 123.2 (s, C$_3$), 120.1 (s, C$_5$), 82.7 (s, C$_{11}$), 81.1 (s, C$_{10}$), 25.6 (s, C$_9$).

3) Preparation of 2-methyl-7-trimethylsilanylethynyl-quinoline

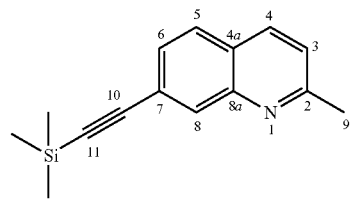

In a sealed tube were introduced 7-bromo-2-methyl-quinoline (500 mg, 2.25 mmol, 1.0 eq), PdCl$_2$(PPh$_3$)$_3$ (79 mg, 0.11 mmol, 5% mol), copper iodide (21 mg, 0.11 mmol, 5% mol), and triphenylphosphine (106 mg, 0.39 mmol, 20% mol). Then, DMF (5 mL) was added followed by diethylamine (3.5 mL, 34 mmol, 15 eq) and trimethylsilylacetylene (350 µL, 2.5 mmol, 1.1 eq). The mixture was heated at 110° C. overnight. After cooling down the solvent was evaporated and the crude product was purified by column chromatography (Florisil, Cyclohexane-EtOAc 95:5) to afford 2-methyl-7-trimethylsilanylethynyl-quinoline as a white solid (435 mg, 81%).

Molecular formula: $C_{15}H_{17}NSi$
Molecular weight: 239.39 g·mol$^{-1}$
$R_f$=0.34 (Cyclohexane/EtOAc: 95/5).
Mp: 96° C.
$^1$H NMR (250 MHz): δ 8.15 (s, 1H, H$_8$), 8.00 (d, J=8.2 Hz, 1H, H$_4$), 7.69 (d, J=8.2 Hz, 1H, H$_5$), 7.52 (d, J=8.2 Hz, 1H, H$_6$), 7.28 (d, J=8.2 Hz, 1H, H$_3$), 2.75 (s, 3H, H$_9$), 0.30 (s, 9H, TMS).
$^{13}$C NMR (63 MHz): δ 160.1 (s, C$_2$), 147.8 (s, C$_{8a}$), 136.1 (s, C$_4$), 132.8 (s, C$_8$), 128.9 (s, C$_6$), 127.8 (s, C$_5$), 126.7 (s, C$_{4a}$), 124.5 (s, C$_7$), 122.9 (s, H$_3$), 105.2 (s, C$_{10}$), 96.5 (s, C$_{11}$), 25.8 (s, C$_9$), 0.40 (s, TMS).

4) Preparation of 7-ethynyl-2-methyl-quinoline

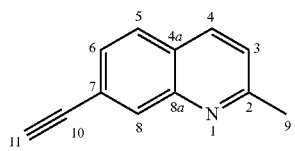

To a solution of 2-methyl-7-trimethylsilanylethynyl-quinoline (140 mg, 0.59 mmol, 1.0 eq) in solution in MeOH (5 mL) was added K$_2$CO$_3$ (324 mg, 2.34 mmol, 4 eq), and the resulting mixture was stirred overnight at room temperature. The solvent was then removed under reduced pressure and water was then added. The aqueous layer was extracted twice with cyclohexane, and then the combined organic layers were washed with brine and dried over MgSO$_4$. After filtration and concentration under reduced pressure the crude product was purified by column chromatography on silica gel (Cyclohexane-EtOAc 99:1) to afford 84 mg of 7-ethynyl-2-methyl-quinoline as a yellow crystal (86%).

Molecular formula: $C_{12}H_9N$
Molecular weight: 167.21 g·mol$^{-1}$
$R_f$=0.35 (Cyclohexane/EtOAc:4/1).
Mp: 41° C.
$^1$H NMR (500 MHz): δ 8.19 (s, 1H, H$_8$), 8.01 (d, J=8.5 Hz, 1H, H$_4$), 7.71 (d, J=8.5 Hz, 1H, H$_5$), 7.54 (d, J=8.5 Hz, 1H, H$_6$), 7.29 (d, J=8.5 Hz, 1H, H$_3$), 3.23 (s, 1H, H$_{11}$), 2.75 (s, 3H, H$_9$).
$^{13}$C NMR (125 MHz): δ 161.3 (s, C$_2$), 148.7 (s, C$_{8a}$), 137.2 (s, C$_4$), 134.1 (s, C$_8$), 129.9 (s, C$_6$), 129.0 (s, C$_5$), 127.9 (s, C$_{4a}$), 124.5 (s, C$_7$), 124.1 (s, C$_3$), 84.8 (s, C$_{10}$), 80.1 (s, C$_{11}$), 26.7 (s, C$_9$).

5) Preparation of 2-methyl-6-trimethylsilanylethynyl-quinoline

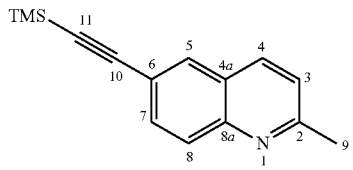 [SMILES: Cc1ccc2cc(C#C[Si](C)(C)C)ccc2n1]

In a sealed tube were introduced 6-bromo-2-methyl-quinoline (4.6 g, 21 mmol, 1 eq), PdCl$_2$(PPh$_3$)$_3$ (727 mg, 1 mmol, 5% mol), copper iodide (197 mg, 1 mmol, 5% mol), and triphenylphosphine (1.1 g, 4.1 mmol, 20% mol). Then, DMF (35 mL) was added followed by diethylamine (6 mL, 62 mmol, 5 eq) and trimethylsilylacetylene (3.2 mL, 23 mmol, 1.1 eq). The mixture was refluxed overnight. After cooling down the solvent was evaporated and the crude product was purified by column chromatography (Florisil, Cyclohexane-AcOEt 95/5) and obtained as a white solid (4.2 g, 83%).

Molecular formula: $C_{15}H_{17}NSi$
Molecular weight: 239.39 g·mol$^{-1}$
$R_f$=0.4 (Cyclohexane/EtOAc:4/1).
$^1$H NMR (250 MHz): δ 7.98 (d, J=8.0 Hz, 1H, H$_8$), 7.94 (d, J=8.5 Hz, 1H, H$_4$), 7.30 (m, 3H, H$_3$, H$_5$ et H$_6$), 2.75 (s, 3H, H$_9$), 0.31 (s, 9H, TMS).

6) Preparation of 6-ethynyl-2-methyl-quinoline

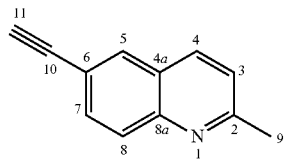

To a solution of 2-methyl-6-trimethylsilanylethynyl-quinoline (2.1 g, 1.03 mmol, 1 eq) in solution in MeOH (5 mL) was added K$_2$CO$_3$ (5.69 g, 4.12 mmol, 4 eq), and the resulting mixture was stirred overnight at room temperature. The solvent was then removed under reduced pressure and water was then added. The aqueous layer was extracted twice with cyclohexane, and then the combined organic layers were washed with brine and dried over MgSO$_4$. After filtration and concentration under reduced pressure the crude product was purified by column chromatography on silica gel (Cyclohexane-EtOAc 99:1) to afford 169 mg of 6-ethynyl-2-methyl-quinoline as a yellow crystal (98%).

Molecular formula: $C_{12}H_9N$
Molecular weight: 167.21 g·mol$^{-1}$
$^1$H NMR (500 MHz): δ 7.94 (d, J=8.5 Hz, 1H, H$_8$), 7.93 (d, J=8.0 Hz, 1H, H$_4$), 7.90 (d, J=1.0 Hz, 1H, H$_5$), 7.70 (dd, J=8.5 Hz, J=1.0 Hz, 1H, H$_7$), 7.25 (d, J=8.0 Hz, 1H, H$_3$), 3.16 (s, 1H, H$_{11}$), 2.72 (s, 3H, H$_9$).
$^{13}$C NMR (125 MHz): δ 161.4 (s, C$_2$), 148.8 (s, C$_{8a}$), 137.2 (s, C$_4$), 133.7 (s, C$_7$), 133.1 (s, C$_5$), 130.3 (s, C$_8$), 127.4 (s, C$_{4a}$), 124.1 (s, C$_3$), 120.8 (s, C$_6$), 84.7 (s, C$_{10}$), 79.4 (s, C$_{11}$), 26.8 (s, C$_9$).

7) Preparation of tris-[4-(2-methyl-quinolin-6-yl-ethynyl)-phenyl]-amine

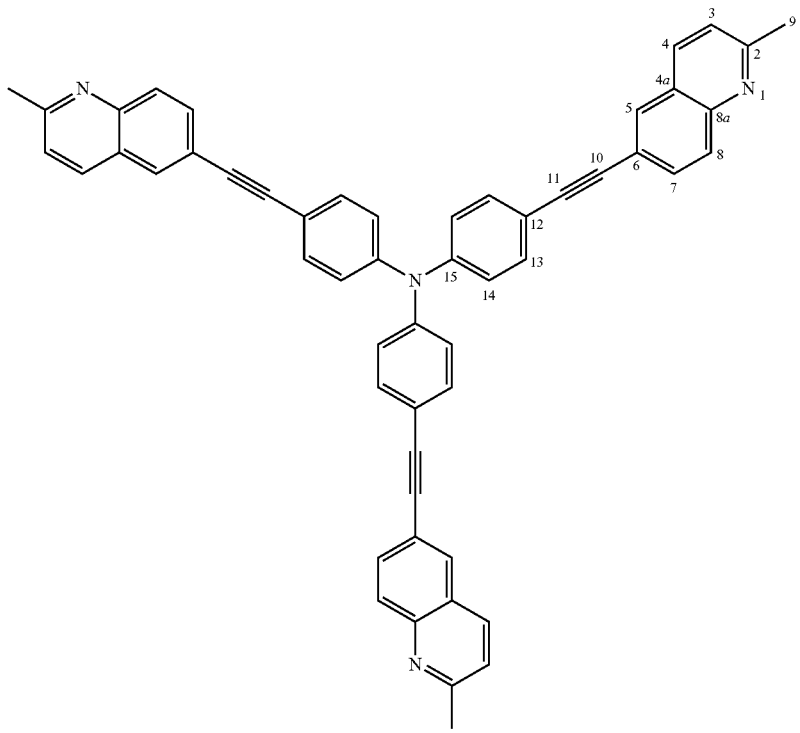

In a schlenk were introduced tris-p-bromophenylamine (54 mg, 0.1 mmol, 1 eq), alkyne derivative (60 mg, 0.4 mmol, 4 eq), PdCl$_2$(PPh$_3$)$_3$ (12 mg, 0.02 mmol, 15 mol %), copper iodide (3 mg, 0.02 mmol, 15 mol %), and triphenylphosphine (15 mg, 0.06 mmol, 55 mol %). Then DMF (500 μL) was added followed by diethylamine (500 μL, 5 mmol, 45 eq). The mixture was refluxed overnight. After cooling down the solvent was evaporated and the crude product was purified by column chromatography (SiO$_2$, Cyclohexane-AcOEt 9/1), and obtained as an orange solid (16 mg, 20%).

Molecular formula: $C_{54}H_{36}N_4$

Molecular weight: 740.89 g·mol$^{-1}$ $^1$H NMR (500 MHz): δ 8.00 (d, J=7.0 Hz, 3H, H$_8$), 7.98 (d, J=8.5 Hz, 3H, H$_4$), 7.95 (d, J=1.5 Hz, 3H, H$_5$), 7.77 (dd, J=7.0 Hz, J=1.5 Hz, 3H, H$_7$), 7.55 (dd, J=7.5 Hz, J=2.0 Hz, 6H, H$_{13}$), 7.35 (dd, J=7.5 Hz, J=1.5 Hz, 6H, H$_{14}$), 7.55 (d, J=8.5 Hz, 3H, H$_3$), 2.74 (s, 9H, H$_9$).

$^{13}$C NMR (125 MHz): δ 161.1 (s, C$_2$), 137.4 (s, C$_{8a}$), 133.7 (s, C$_{15}$), 133.5 (s, C$_4$), 133.1 (s, C$_{13}$), 132.2 (s, C$_7$), 130.0 (s, C$_5$), 129.9 (s, C$_8$), 129.8 (s, C$_{14}$), 127.7 (s, C$_{4a}$), 124.5 (s, C$_6$), 124.1 (s, C$_3$), 122.2 (s, C$_{12}$), 91.7 (s, C$_{10}$), 90.5 (s, C$_{11}$), 26.7 (s, C$_9$).

ESI m/z: 741.0 (M+H$^+$).

8) Preparation of tris-[4-(quinolin-2-carbaldehyde-6-ylethynyl)-phenyl]amine

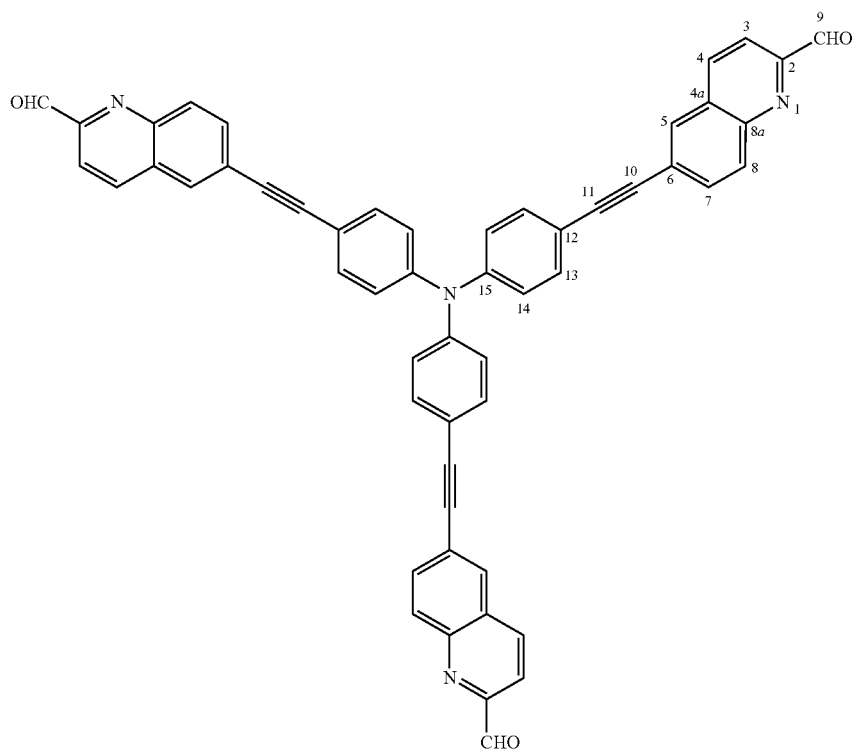 [SMILES: O=Cc1ccc2cc(C#Cc3ccc(N(c4ccc(C#Cc5ccc6nc(C=O)ccc6c5)cc4)c4ccc(C#Cc5ccc6nc(C=O)ccc6c5)cc4)cc3)ccc2n1]

Selenium dioxyde (35 mg, 0.3 mmol, 4 eq) in suspension in dioxane (1 mL) was heated at 60° C. Tris-quinoline derivative (60 mg, 0.08 mmol) was introduced and the mixture was left to react at 80° C. for 12 hours. After cooling to room temperature, the mixture was filtered on celite, eluted with dioxane and concentrated under reduced pressure. The product was obtained as a yellow solid (15 mg, 24%).

Molecular formula: $C_{54}H_{30}N_4O_3$
Molecular weight: 782.84 g·mol$^{-1}$ $^1$H NMR (500 MHz): δ 10.20 (s, 3H, CHO), 8.26 (d, J=8.5 Hz, 3H, H$_4$), 8.20 (d, J=8.5 Hz, 3H, H$_3$), 8.06 (d, J=2.0 Hz, 3H, H$_5$), 8.03 (d, J=8.5 Hz, 3H, H$_8$), 7.89 (dd, J=8.5 Hz, J=2.0 Hz, 3H, H$_7$), 7.57 (m, 6H, Ho), 7.37 (m, 6H, H$_{14}$).

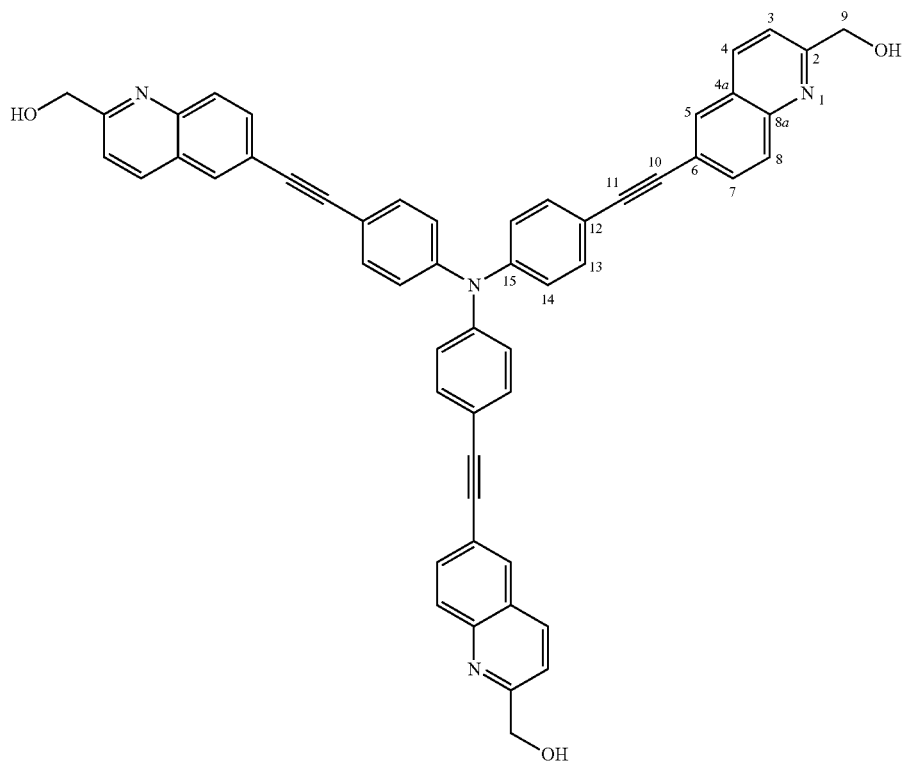 [SMILES: OCc1ccc2cc(C#Cc3ccc(N(c4ccc(C#Cc5ccc6nc(CO)ccc6c5)cc4)c4ccc(C#Cc5ccc6nc(CO)ccc6c5)cc4)cc3)ccc2n1]

In a solution of trialdehyde (20 mg, 0.03 mmol) in EtOH (0.2 mL) at 0° C. sodium borohydride (5 mg, 0.13 mmol, 4.5 eq) was added portionwise and the mixture was stirred at room temperature for 1 hour. The solvent was evaporated and water was added. The solution was extracted with dichloromethane and the organic layer was washed twice with water and brine, dried over $MgSO_4$, and concentrated under reduced pressure. Triol was obtained as a yellow oil.

Molecular formula: $C_{54}H_{36}N_4O_3$

Molecular weight: 788.89 g·mol$^{-1}$

Preparation of Caged Acetate and Glutamate Compounds According to the Invention

D—Preparation of acetic acid 6-[tris-(2-acetoxymethyl-quinolin-6-yl)-amino]-quinolin-2-ylmethyl ester

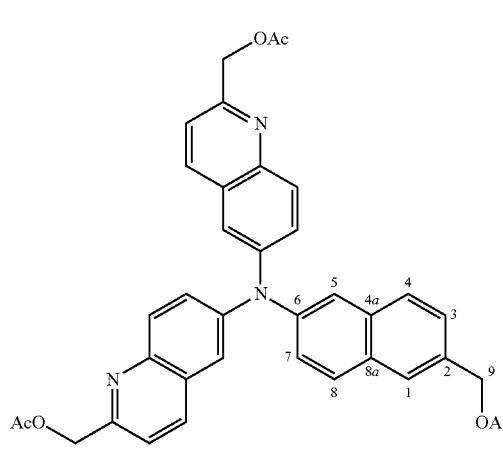

Triol (11 mg, 0.02 mmol), triethylamine (14 µL, 0.1 mmol, 4.5 eq), acetic anhydride (10 µL, 0.1 mmol, 4.5 eq) and a catalytic amount of DMAP were dissolved in dichloromethane (100 µL) and the mixture was stirred at room temperature for 2 hours in the dark. The crude product was the purified by column chromatography (SiO$_2$, Dichloromethane-MeOH 95/5), and obtained as a yellow oil (6 mg, 43%).

Molecular formula: C$_{36}$H$_{30}$N$_4$O$_6$

Molecular weight: 614.65 g·mol$^{-1}$

R$_f$=0.21 (Cyclohexane/EtOAc:1/3).

$^1$H NMR (500 MHz): δ 8.01 (d, J=9.0 Hz, 3H, H$_8$), 7.90 (d, J=8.5 Hz, 3H, H$_4$), 7.58 (dd, J=9.0 Hz, J=2.5 Hz, 3H, H$_7$), 7.43 (d, J=2.5 Hz, 3H, H$_5$), 7.39 (d, J=8.5 Hz, 3H, H$_3$), 5.34 (s, 6H, H$_9$), 2.15 (s, 9H, OAc).

$^{13}$C NMR (125 MHz): δ 172.0 (s, CO), 156.6 (s, C$_2$), 146.8 (s, C$_6$), 146.5 (s, C$_{8a}$), 137.3 (s, C$_4$), 132.1 (s, C$_7$), 130.0 (s, C$_{4a}$), 129.5 (s, C$_8$), 121.6 (s, C$_3$C$_5$), 68.8 (s, C$_9$), 22.3 (s, OAc).

MS (ESI): m/z=615.3 [M+H]$^+$.

HRMS (ESI): m/z calculated for [C$_{36}$H$_{30}$N$_4$O$_6$+H]$^+$ 615.2244, found 615.2233 (ppm −1.7).

UV (MeCN): λ$_{max}$=366 nm, ε(λ$_{max}$)=13900 M$^{-1}$·cm$^{-1}$.

E—Preparation of acetic acid 7-[tris-(2-acetoxymethyl-quinolin-7-yl)-amino]-quinolin-2-ylmethyl ester

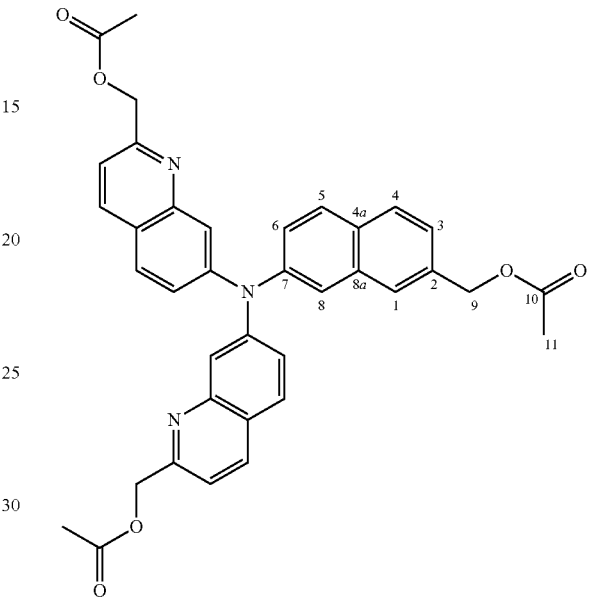

Triol (15 mg, 0.03 mmol), triethylamine (19 µL, 0.1 mmol, 4.5 eq), acetic anhydride (13 µL, 0.1 mmol, 4.5 eq) and a catalytic amount of DMAP were dissolved in dichloromethane (100 µL) and the mixture was stirred at room temperature for 2 hours in the dark. The crude product was the purified by column chromatography (SiO$_2$, Dichloromethane-MeOH 95/5) and obtained as a yellow oil (12 mg, 67%).

Molecular formula: C$_{36}$H$_{30}$N$_4$O$_6$

Molecular weight: 614.65 g·mol$^{-1}$

R$_f$=0.23 (Cyclohexane/EtOAc:1/1), 0.55 (Cyclohexane/EtOAc: 1/3).

$^1$H NMR (500 MHz): δ 8.09 (d, J=8.5 Hz, 1H, H$_4$), 7.73 (s, 1H, H$_8$), 7.72 (d, J=8.5 Hz, 1H, H$_5$), 7.44 (dd, J=8.5 Hz, J=2.0 Hz, 1H, H$_6$), 7.36 (d, J=8.5 Hz, 1H, H$_3$), 5.28 (s, 2H, H$_9$).

$^{13}$C NMR (125 MHz): δ 170.5 (s, C$_{10}$), 156.6 (s, C$_2$), 148.8 (s, C$_{8a}$), 148.2 (s, C$_7$), 136.4 (s, C$_4$), 128.8 (s, C$_5$), 124.9 (s, C$_3$), 124.6 (s, C$_{4a}$), 122.4 (s, C$_6$), 118.5 (s, C$_8$), 67.2 (s, C$_9$), 27.0 (s, C$_{11}$).

MS (ESI): m/z=615.1 [M+H]$^+$, 1229.0 [2M+H]$^+$.

HRMS (ESI): m/z calculated for [C$_{36}$H$_{30}$N$_4$O$_6$+H]$^+$ 615.2244, found 615.2221 (ppm −3.7).

HPLC-MS: (Method C): rt=16.13 min, m/z=615.1, extraction at 260 and 360 nm, λ$_{max}$=367 nm.

UV (MeCN): λ$_{max}$=367 nm, ε(λ$_{max}$)=13700 M$^{-1}$·cm$^{-1}$.

F—Preparation of 2-amino-pentanedioic acid 5-(7-{tris-[2-(4-amino-4-carboxy-butyryloxymethyl)-quinolin-7-yl]-amino}-quinoline-2-ylmethyl)ester

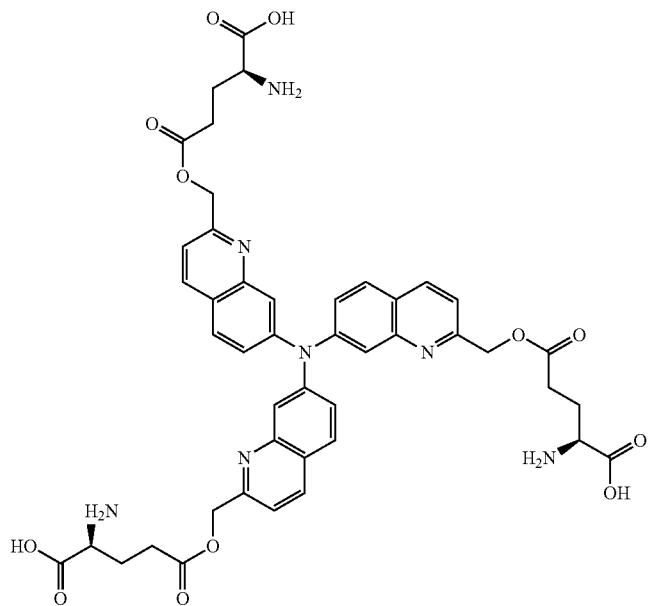 [SMILES: N[C@@H](CCC(=O)OCc1ccc2ccc(N(c3ccc4ccc(COC(=O)CC[C@H](N)C(=O)O)nc4c3)c3ccc4ccc(COC(=O)CC[C@H](N)C(=O)O)nc4c3)cc2n1)C(=O)O]

The NHBOC tert-butyl ester protected triglutamate (12 mg, 0.014 mmol) was dissolved in a solution of 50% of TFA in dichloromethane and the medium was stirred at room temperature during 3 hours in the dark. After the reaction was completed, the solvent was evaporated and the resulting salt was crystallized from MeOH and ether, and then filtered and washed with ether, to an orange powder (7 mg, 95%).

Molecular formula: $C_{45}H_{45}N_7O_{12}$

Molecular weight: 875.88 g·mol$^{-1}$ $^1$H NMR (500 MHz): δ 8.43 (d, J=8.0 Hz, 3H, H$_4$), 8.02 (d, J=8.0 Hz, 3H, H$_5$), 7.76 (s, 3H, H$_8$), 7.59 (d, J=8.0 Hz, 6H, H$_3$ and H$_6$), 5.38 (s, 6H, H$_9$), 4.04 (s, 3H, H$_{13}$), 2.75 (m, 6H, H$_{12}$), 2.22 (m, 6H, H$_{11}$).

MS (ESI): m/z=876.1 [M+H]$^+$, ESI –: 874.0 [M–H]$^+$.

HRMS (ESI): m/z calculated for $[C_{45}H_{45}N_7O_{12}+H]^+$ 876.3204, found 876.3236 (ppm 3.6).

HPLC-MS: (Method C): rt=15.41 min, m/z=876.1 [M+H]$^+$, extraction at 260 and 360 nm, λ$_{max}$=396 nm.

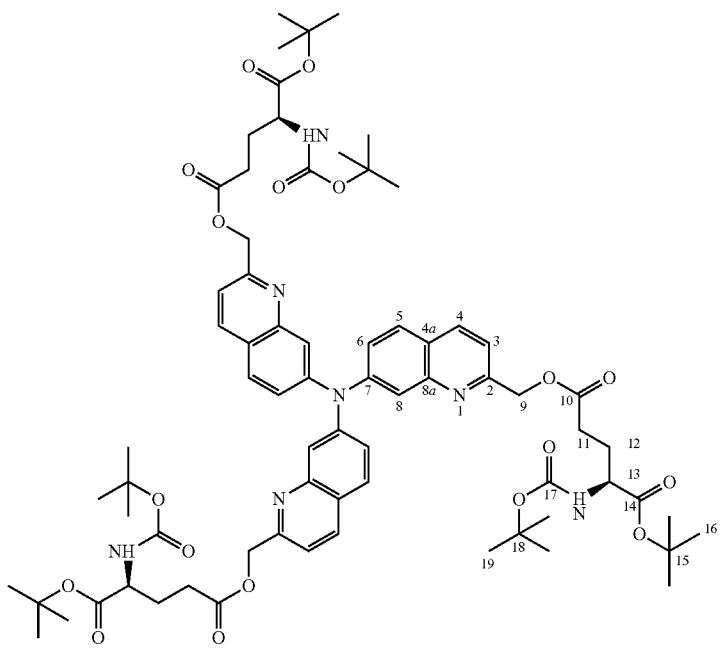 [SMILES: CC(C)(C)OC(=O)N[C@@H](CCC(=O)OCc1ccc2ccc(N(c3ccc4ccc(COC(=O)CC[C@H](NC(=O)OC(C)(C)C)C(=O)OC(C)(C)C)nc4c3)c3ccc4ccc(COC(=O)CC[C@H](NC(=O)OC(C)(C)C)C(=O)OC(C)(C)C)nc4c3)cc2n1)C(=O)OC(C)(C)C]

The NHBOC tert-butyl ester protected triglutamate (2 mg, 0.002 mmol) obtained (see formula here-above) was dissolved in a solution of 99% TFA/Dichloromethane 1/4 and the medium was stirred at room temperature during 4 hours in the dark. After the reaction was completed, the solvent was evaporated and the resulting HCl salt was dried and stored at −4° C. before use.

Molecular formula: $C_{45}H_{45}N_7O_{12}$

Molecular weight: 875.88 g·mol$^{-1}$ $R_f$=0.21 (Cyclohexane/EtOAc: 1/1).

$^1$H NMR (500 MHz): δ 8.08 (d, J=8.5 Hz, 3H, $H_4$), 7.72 (d, J=8.5 Hz, 3H, $H_5$), 7.71 (s, 3H, $H_8$), 7.43 (dd, J=8.5 Hz, J=2.5 Hz, 3H, $H_6$), 7.36 (d, J=8.5 Hz, 3H, $H_3$), 5.28 (s, 6H, $H_9$), 4.18 (s, 3H, $H_{13}$), 2.48 (m, 6H, $H_{12}$), 1.93 (m, 6H, $H_{11}$), 1.42 (s, $H_{19}$ rotamer), 1.41 (s, 27H, $H_{19}$), 1.40 (s, $H_{16}$ rotamer), 1.38 (s, 27H, $H_{16}$).

$^{13}$C NMR (125 MHz): δ 173.8 (s, $C_{10}$), 172.6 (s, $C_{14}$), 158.1 (s, $C_2$), 156.8 (s, $C_{17}$), 149.6 (s, $C_{8a}$), 138.0 (s, $C_7$), 130.3 (s, $C_4$), 126.4 (s, $C_5$), 126.2 (s, $C_3$), 123.7 (s, $C_{4a}$), 119.9 (s, $C_6$), 119.8 (s, $C_8$), 81.1 (s, $C_{18}$), 78.8 (s, $C_{15}$), 68.7 (s, $C_9$), 50.6 (s, $C_{13}$), 29.7 (s, $C_{19}$), 29.5 (s, $C_{16}$), 27.0 (s, $C_{11}$), 26.3 (s, $C_{12}$).

MS (ESI): m/z=1344.5 [M+H]$^+$, 1366.3 [M+Na]$^+$.

HRMS (ESI): m/z calcd for $[C_{72}H_{93}N_7O_{18}+Na]^+$ 1366.6475, found 1366.6475 (ppm 0.0).

G—Preparation of 6,6',6''-(4,4',4''-nitrilotris(benzene-4,1-diyl)tris(ethyne-2,1-diyl)tris(2-((tert-butyldimethylsilyloxy)methyl)-7-(dimethylamino)quinoline-8-carbonitrile)

1) Preparation of 6-bromo-7-dimethylamino-2-methylquinoline-8-carbonitrile

To a solution of 8-cyano-7-N,N-dimethylaminoquinaldine (1.1 g, 5.2 mmol, 1.0 eq) in chloroform (26 mL) was added NBS (1.2 g, 6.8 mmol, 1.3 eq) and the solution was stirred at room temperature for 3 hours. Then, the mixture was washed twice with a saturated solution of $Na_2S_2O_3$ and a saturated solution of NaCl, and the organic layer was dried over $MgSO_4$, filtered, and concentrated under reduced pressure. The 6-Bromo-7-dimethylamino-2-methylquinoline-8-carbonitrile was crystallized from ether and obtained as pale yellow crystal (1.2 g, 78%).

Molecular formula: $C_{13}H_{12}BrN_3$

Molecular weight: 290.16 g·mol$^{-1}$ $R_f$=0.6 (Cyclohexane/EtOAc:4/1).

$^1$H NMR (500 MHz): δ 7.73 (s, 1H, $H_5$), 7.30 (d, J=9.0 Hz, 1H, $H_4$), 6.82 (d, J=9.0 Hz, 1H, $H_3$), 3.15 (s, 6H, $H_{10}$), 2.59 (s, 3H, $H_9$).

$^{13}$C NMR (125 MHz): δ 160.1 (s, $C_2$), 157.5 (s, $C_7$), 150.2 (s, $C_{8a}$), 139.0 (s, $C_4$), 132.1 (s, $C_5$), 121.7 (s, $C_{4a}$), 119.8 (s, CN), 118.8 (s, $C_3$), 117.0 (s, $C_6$), 92.4 (s, $C_8$), 44.2 (s, $C_{10}$), 27.4 (s, $C_9$).

MS (ESI): m/z=290.0, 292.0 [M+H]$^+$.

HRMS (ESI): m/z calculated for [$C_{13}H_{12}BrN_3$+H]$^+$ 290.0293, found 290.0291 (ppm −0.6); 292.0272, found 292.0277 (ppm 1.6).

2) Preparation of 6-bromo-7-dimethylamino-2-formylquinolin-8-carbonitrile

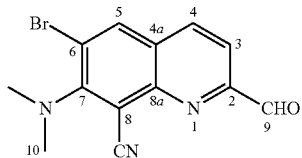

Selenium dioxyde (50 mg, 0.45 mmol, 1.3 eq) in suspension in dioxane (1 mL) was heated at 60° C. The 6-bromo-7-dimethylamino-2-methylquinoline-8-carbonitrile (100 mg, 0.34 mmol, 1.0 eq) was then introduced and the mixture was left to react at 80° C. for 3 hours. After cooling to room temperature, the mixture was filtered on celite, eluted with dioxane and concentrated under reduced pressure. The crude product was precipitated from ether to afford 6-bromo-7-dimethylamino-2-formylquinolin-8-carbonitrile as an orange powder (74 mg, 72%).

Molecular formula: $C_{13}H_{10}BrN_3O$
Molecular weight: 304.14 g·mol$^{-1}$
MS (ESI): m/z=304.0, 306.0 [M+H]$^+$, 336.0, 338.0 [hemiacetal+H]$^+$.

3) Preparation of 6-bromo-7-dimethylamino-2-(hydroxymethyl)quinoline-8-carbonitrile

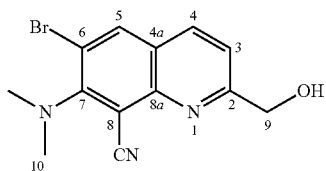 [SMILES: CN(C)c1c(Br)cc2ccc(CO)nc2c1C#N]

The 6-bromo-7-dimethylamino-2-formylquinolin-8-carbonitrile (2.4 g, 7.9 mmol, 1.0 eq) was added to MeOH (20 mL) at 0° C. Sodium borohydride (328 mg, 8.7 mmol, 1.1 eq) was then introduced and the mixture was stirred at room temperature for 1 hour. The solution was quenched with HCl 1 M, ethanol was evaporated and water was added. The solution was extracted with dichloromethane and the organic layer was washed twice with water and brine, dried over MgSO$_4$, filtered and concentrated under reduced pressure. The 6-bromo-7-dimethylamino-2-(hydroxymethyl)quinoline-8-carbonitrile was obtained as an orange solid (2.4 g, 98%).

Molecular formula: $C_{13}H_{12}BrN_3O$
Molecular weight: 306.16 g·mol$^{-1}$
$R_f$=0.55 (Cyclohexane/EtOAc: 1/1).

$^1$H NMR (250 MHz): δ 8.06 (s, 1H, $H_5$), 7.63 (d, J=9.5 Hz, 1H, $H_4$), 7.13 (d, J=9.5 Hz, 1H, $H_3$), 4.83 (s, 2H, $H_9$), 3.38 (s, 6H, $H_{10}$).

$^{13}$C NMR (63 MHz): δ 158.3 (s, $C_2$), 156.4 (s, $C_7$), 148.0 (s, $C_{8a}$), 138.8 (s, $C_4$), 131.3 (s, $C_5$), 121.4 (s, $C_3$), 118.5 (s, $C_{4a}$), 118.2 (s, CN), 112.6 (s, $C_6$), 91.0 (s, $C_8$), 64.0 (s, $C_9$), 43.1 (s, $C_{10}$).

MS (ESI): m/z=306.0, 308.0 [M+H]$^+$.

HRMS (ESI): m/z calculated for [$C_{13}H_{12}BrN_3O$+H]$^+$ 306.0242, found 306.0252 (ppm 3.3); 308.0222, found 308.0230 (ppm 2.8).

4) Preparation of 6-bromo-2-((tert-butyldimethylsilyloxy)methyl)-7-(dimethylamino)quinoline-8-carbonitrile

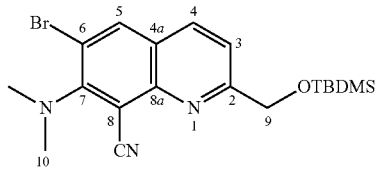

The 6-bromo-7-dimethylamino-2-(hydroxymethyl)quinoline-8-carbonitrile (2 g, 6.5 mmol, 1 eq), TBDMSCl (1.4 g, 7.3 mmol, 1.1 eq) and imidazole (623 mg, 7.3 mmol, 1.1 eq) were added to DMF (20 mL). The resulting solution was stirred at room temperature for 3 hours, and then the solvent was removed under high reduced pressure. Cyclohexane was added and the mixture was washed twice with water, and then with brine. The organic layer was then dried over MgSO$_4$, and concentrated under reduced pressure. The product was obtained pure as a yellow powder (1.9 g, 68%).

Molecular formula: $C_{19}H_{26}BrN_3OSi$
Molecular weight: 420.42 g·mol$^{-1}$
$R_f$=0.23 (Cyclohexane/EtOAc: 3/1).

5) Preparation of 2-((tert-butyldimethylsilyloxy)methyl)-7-(dimethylamino)-6-(trimethylsilyl)ethynyl) quinoline-8-carbonitrile

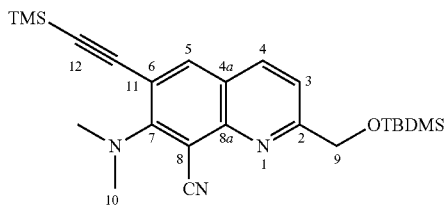 [SMILES: CN(C)c1c(C#C[Si](C)(C)C)cc2ccc(CO[Si](C)(C)C(C)(C)C)nc2c1C#N]

In a sealed tube were introduced the 6-bromo-2-((tert-butyldimethylsilyloxy)methyl)-7-(dimethylamino)quinoline-8-carbonitrile (946 mg, 2.25 mmol, 1.0 eq), $PdCl_2$ $(PPh_3)_3$ (79 mg, 0.11 mmol, 5% mol), copper iodide (21 mg, 0.11 mmol, 5% mol), and triphenylphosphine (106 mg, 0.39 mmol, 20% mol). Then, DMF (5 mL) was added followed by diethylamine (3.5 mL, 34 mmol, 15 eq) and trimethylsilylacetylene (350 μL, 2.5 mmol, 1.1 eq). The mixture was heated at 110° C. overnight. After cooling down the solvent was evaporated and the crude product was purified by column chromatography (Florisil, Cyclohexane-EtOAc 95:5) to afford 2-((tert-butyldimethylsilyloxy)methyl)-7-(dimethylamino)-6-(trimethylsilyl)ethynyl)quinoline-8-carbonitrile as a white solid (700 mg, 71%).

Molecular formula: $C_{24}H_{35}N_3OSi_2$
Molecular weight: 437.73 g·mol$^{-1}$ $^1$H NMR (500 MHz): δ 7.95 (s, 1H, $H_5$), 7.65 (d, J=9.5 Hz, 1H, $H_4$), 7.03 (d, J=9.5 Hz, 1H, $H_3$), 5.00 (s, 2H, $H_9$), 3.28 (s, 6H, $H_{10}$), 0.97 (s, 9H, TBDMS), 0.29 (s, 9H, TMS), 0.17 (s, 6H, TBDMS).

6) Preparation of 2-((tert-butyldimethylsilyloxy)methyl)-7-(dimethylamino)-6-ethynylquinoline-8-carbonitrile

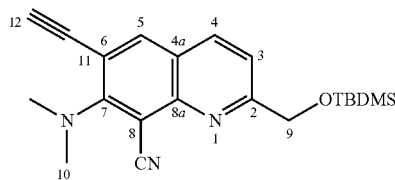 [SMILES: C#Cc1cc2ccc(CO[Si](C)(C)C(C)(C)C)nc2c(C#N)c1N(C)C]

To a solution of 2-((tert-butyldimethylsilyloxy)methyl)-7-(dimethylamino)-6-(trimethylsilyl)ethynyl)quinoline-8-carbonitrile (263 mg, 0.6 mmol, 1 eq) in solution in MeOH (5 mL) was added $K_2CO_3$ (324 mg, 2.3 mmol, 4 eq), and the resulting mixture was stirred overnight at room temperature. The solvent was then removed under reduced pressure and water was then added. The aqueous layer was extracted twice with cyclohexane, then the combined organic layers were washed with brine and dried over $MgSO_4$. A white solid was obtained as the pure product after concentration under reduced pressure (189 mg, 86%).

Molecular formula: $C_{21}H_{27}N_3OSi$ Molecular weight: 365.54 g·mol$^{-1}$ $R_f$=0.22 (Cyclohexane/EtOAc: 4/1).

$^1$H NMR (500 MHz): δ 8.03 (s, 1H, $H_5$), 7.62 (d, J=9.5 Hz, 1H, $H_4$), 7.09 (d, J=9.5 Hz, 1H, $H_3$), 5.12 (s, 2H, $H_9$), 3.34 (s, 6H, $H_{10}$), 0.97 (s, 9H, TBDMS), 0.20 (s, 6H, TBDMS).

$^{13}$C NMR (125 MHz): δ 163.9 (s, $C_2$), 158.2 (s, $C_7$), 151.0 (s, $C_{8a}$), 141.6 (s, $C_5$), 132.8 (s, $C_4$), 120.6 (s, $C_{4a}$), 119.6 (s, $C_3$), 119.2 (s, CN), 114.1 (s, $C_6$), 94.1 (s, $C_8$), 84.2 (s, $C_{11}$), 81.4 (s, $C_{12}$), 67.7 (s, $C_9$), 44.2 (s, $C_{10}$), 27.4 (s, TBDMS), 20.0 (s, TBDMS), −3.6 (s, TBDMS).

7) Preparation of 6,6',6''-(4,4',4''-nitrilotris(benzene-4,1-diyl)tris(ethyn-2,1-diyl))tris(2-((tert-butyldimethylsilyloxy)methyl)-7-(dimethylamino)quinoline-8-carbonitrile

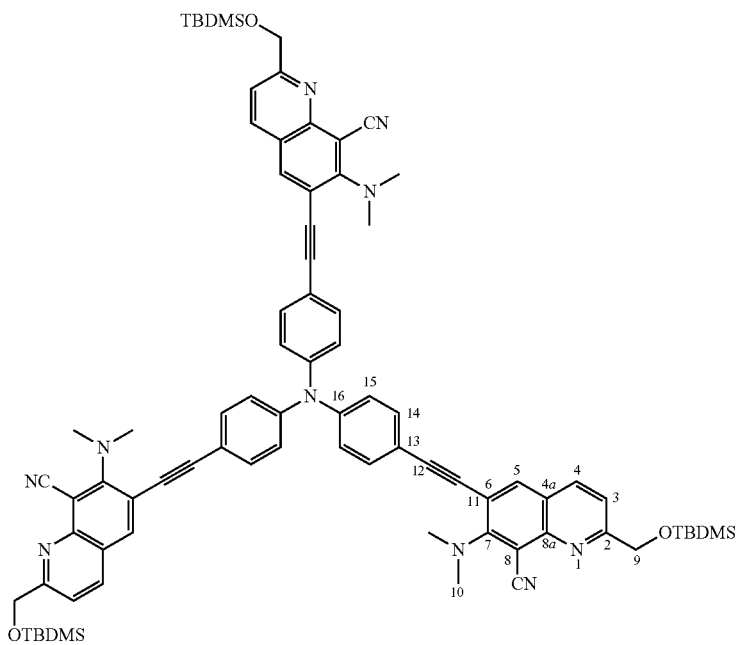 [SMILES: CN(C)c1c(C#Cc2ccc(N(c3ccc(C#Cc4cc5ccc(CO[Si](C)(C)C(C)(C)C)nc5c(C#N)c4N(C)C)cc3)c3ccc(C#Cc4cc5ccc(CO[Si](C)(C)C(C)(C)C)nc5c(C#N)c4N(C)C)cc3)cc2)cc2ccc(CO[Si](C)(C)C(C)(C)C)nc2c1C#N]

In a sealed tube were introduced tris-para-iodophenylamine (62 mg, 0.1 mmol, 1.0 eq), 2-((tert-butyldimethylsilyloxy)methyl)-7-(dimethylamino)-6-ethynylquinoline-8-carbonitrile (110 mg, 0.3 mmol, 3.0 eq), PdCl$_2$(PPh$_3$)$_3$ (11 mg, 0.015 mmol, 15% mol), copper iodide (3 mg, 0.015 mmol, 15% mol), and triphenylphosphine (16 mg, 0.06 mmol, 60% mol). Then, DMF (0.3 mL) was added followed by diethylamine (0.6 mL, 4.5 mmol, 45 eq). The mixture was heated at 110° C. overnight. After cooling down the solvent was evaporated and the crude product was purified by column chromatography (SiO$_2$, Cyclohexane-EtOAc 95:5) to afford 6,6',6"-(4,4',4"-nitrilotris(benzene-4,1-diyl)tris(ethyn-2,1-diyl))tris(2-((tert-butyldimethylsilyloxy)methyl)-7-(dimethylamino)quinoline-8-carbonitrile as an orange oil (39 mg, 29%).

Molecular formula: C$_{81}$H$_{90}$N$_{10}$O$_3$Si$_3$

Molecular weight: 1335.90 g·mol$^{-1}$ $^1$H NMR (250 MHz): δ 8.07 (s, 3H, H$_5$), 7.65 (d, J=9.5 Hz, 3H, H$_4$), 7.50 (d, J=7.8 Hz, 6H, H$_{14}$) 7.14 (m, 9H, H$_{15}$H$_3$), 5.21 (s, 6H, H$_9$), 3.36 (s, 18H, H$_{10}$), 0.93 (s, 27H, TBDMS), 0.22 (s, 18H, TBDMS).

Photolysis Experiments:

Then, the photolysis of the acylated tris-heteroarylamine compounds of the invention under UV and IR conditions was studied. Either the triacetate and the triglutamate esters were examined.

The photochemical efficiency of any chromophores is determined by the extinction coefficient (ε) and the quantum yield (Q$_u$) that is characteristic of the observed photochemical event of the chromophore. The product of these quantities (εQ$_u$) characterizes the efficiency of the event such as fluorescence or chemical transformation, for example by the incident light. The 2PA capacity of a molecule is characterized by the two-photon absorption cross-section δ$_a$, and expressed in GM unit (1 GM=10$^{-50}$ cm$^4$·s·photons$^{-1}$), in honor of Maria Göppert-Mayer. This quantum, that is analogous to ε, reflects the likelihood of the excitation of a molecule by the simultaneous absorption of two photons at a particular wavelength and polarization. The relation between the two-photon absorption cross-section δ$_a$, and the two-photon photolysis uncaging cross-section (δ$_u$) is described by:

$$\delta_u = Q_{u2} \cdot \delta_a$$

wherein Q$_{u2}$ is the two-photon photolysis quantum yield.

As in 1PA the product of Q$_{u2}$·δ$_a$ characterizes thus the efficiency of the TPA process.

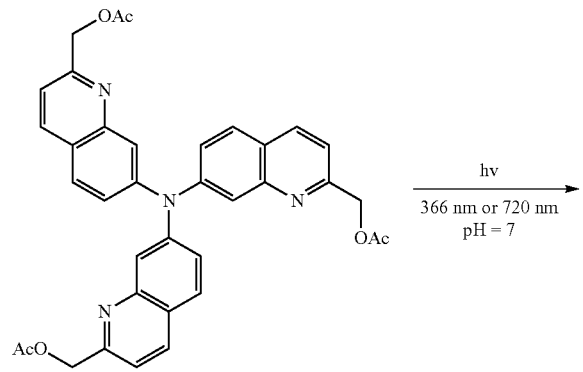

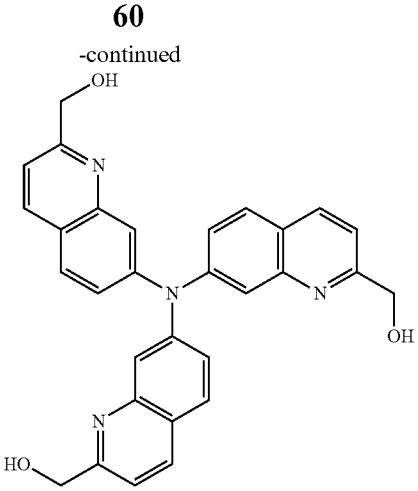

Evaluation of the Compounds of the Invention Under One-Photon (UV) Irradiation Conditions:

Either the triacetate and triglutamate samples were prepared in 0.1 mM concentration either in aqueous TRIS buffer (pH=7), or in a 50/50 mixture of acetonitrile/Britton-Robinson buffer (pH=7). An aliquat (1 mL) of this solution was irradiated at approximately 366 nm (ε$_{366nm}$=13700 M$^{-1}$·cm$^{-1}$, ε being the molar extinction coefficient) in a 1 mL quartz dish. The evolution of the photolysis was followed by HPLC using C-18 reversed phase chromatography (XTerra, eluents: acetonitrile/methanol/NH$_4$CO$_2$H, detection at 260 and 360 nm).

The results obtained for the triacetate compound of the invention, derived from 7-aminoquinaldine trimer, are the following:

t$_{90\%}$=48 min,

Uncaging quantum yield: Q$_u$=0.045, and

Transformation efficiency: εQ$_u$=616.

Evaluation of the Triacetate Compound of the Invention Derived from 7-Aminoquinaldine Trimer Under Two-Photon (IR) Irradiation Conditions:

Samples of 0.1 mM were prepared either in aqueous TRIS buffer (pH=7), or in a mixture (50/50) of acetonitrile/TRIS, and were irradiated as follows in a 45 μL quartz dish. The two-photon photolysis was done using a titanium-sapphire laser (Ti:Sa; Mai Tai, Spectra Physics, Inc., USA), set to 720 nm and provided 100 fs pulses at a repetition rate of 80 MHz. The laser light was tightly focused by a 50 mm lens to a spot of 30 μm diameter (LEICA) on the dish to a spot with a diameter of approximately 900 nm. The laser wavelength used for the two-photon patterning experiments was 720 nm. The maximum time-averaged laser power in the object plane at this wavelength was about 90-100 mW, corresponding to pulse energy of roughly 1.3 nJ. Both the total exposure time and the applied laser power were varied in order to study the effect of the two-photon uncaging on the deprotection.

The results obtained for the compound of the invention are:

δ$_u$=0.12 GM, and

δ$_a$=2.7 GM.

The invention claimed is:

1. A compound of the following formula (I):

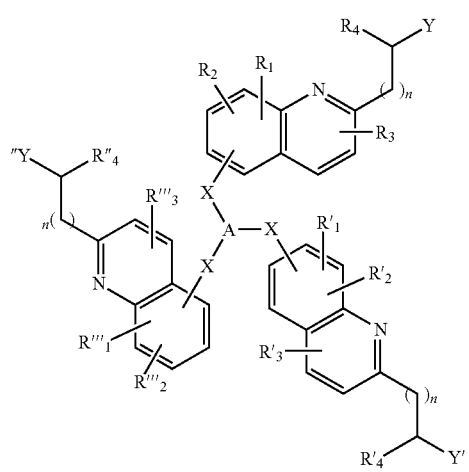

wherein:
n=0 or 1,
A is a nitrogen atom;
X is a direct single bond between A and the quinoline group, an alkyne group —C≡C—, or a

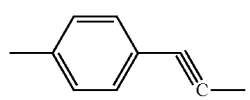

group;

$R_1$, $R'_1$, $R''_1$, $R_2$, $R'_2$, $R''_2$, $R_3$, $R'_3$, $R''_3$, $R_4$, $R'_4$ and $R''_4$ independently are hydrogen, halogen, amine, nitrile, nitro or optionally substituted linear or branched alkyl or alkoxy containing 1 to 30 carbon atoms; and Y, Y' and Y'' independently are OH, OC(O)CH$_3$ or OC(O)CH$_2$CH$_2$CH(NH$_2$)COOH.

2. A compound according to claim 1 of the following formula:

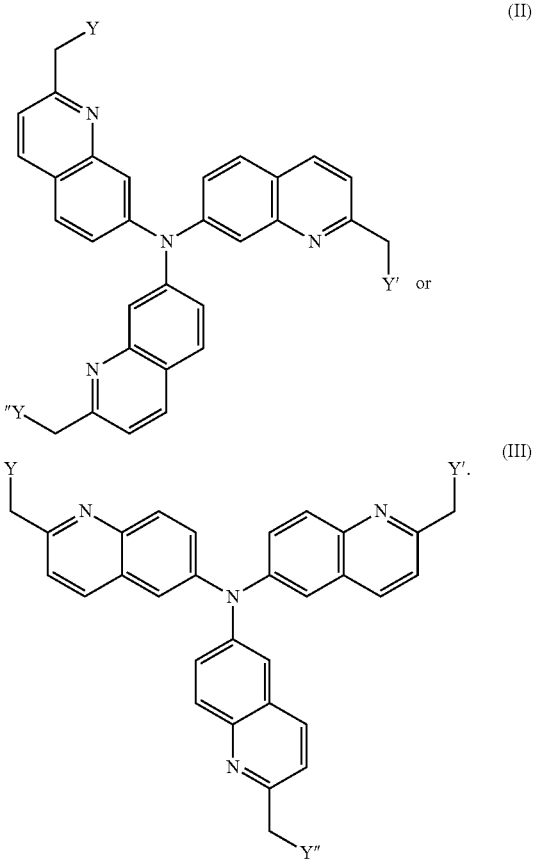

3. A compound according to claim 1 of the following formula:

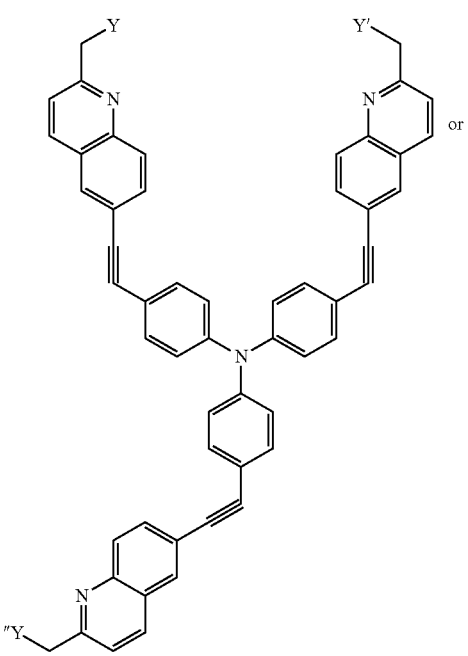

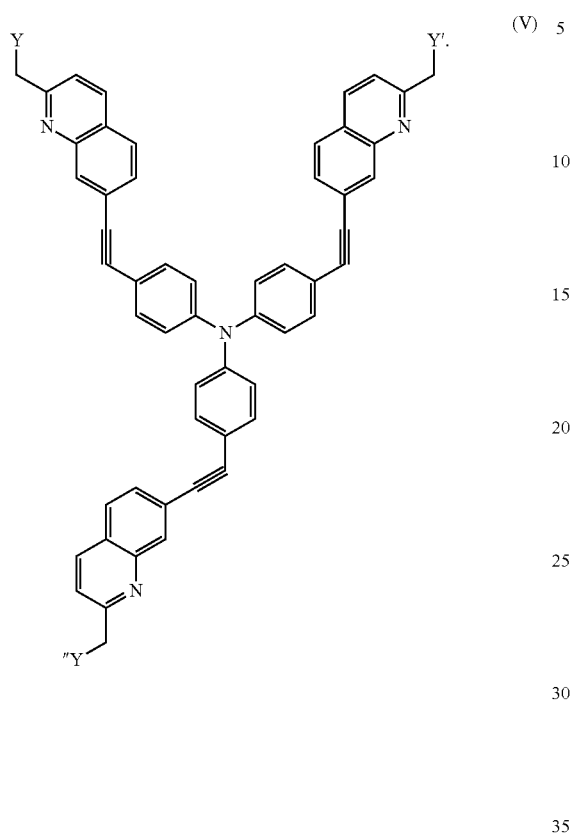
4. A compound according to claim 1 selected from the following compounds:
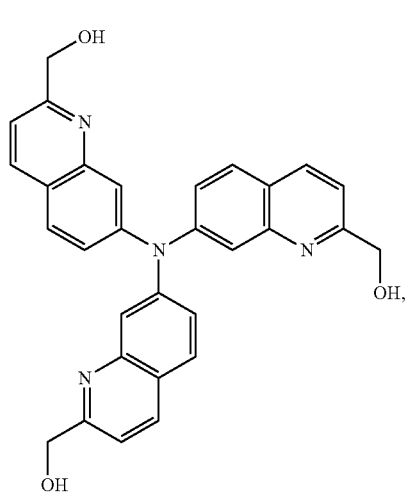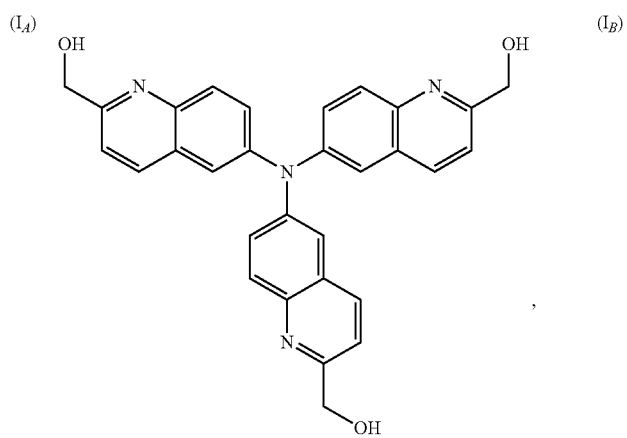

-continued
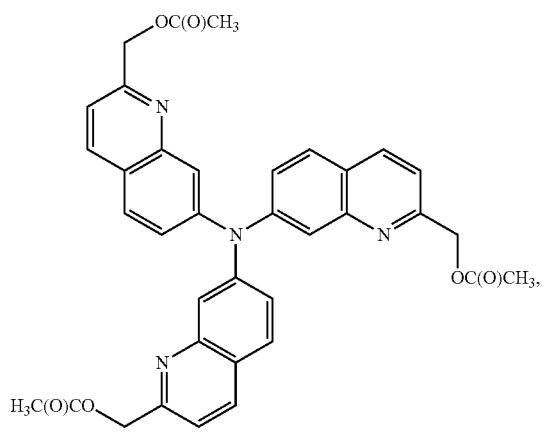
(I_C)
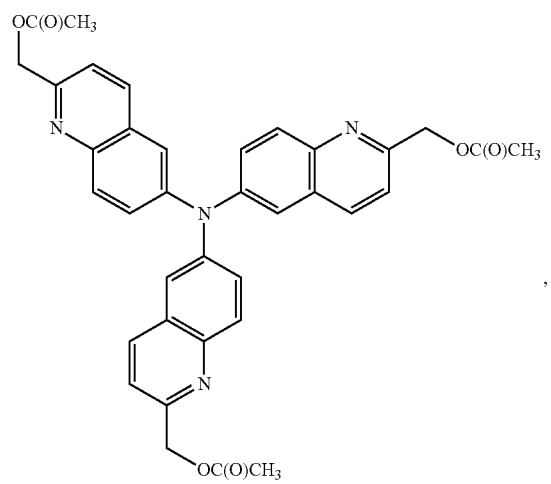
(I_D)
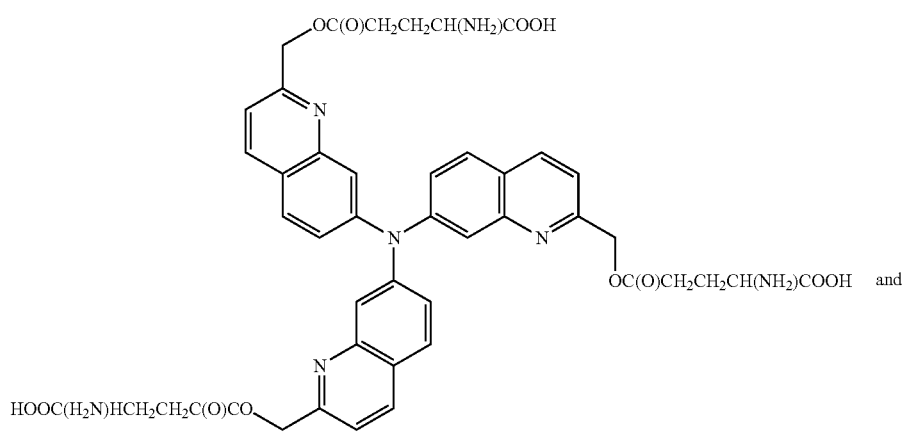
(I_E)
and
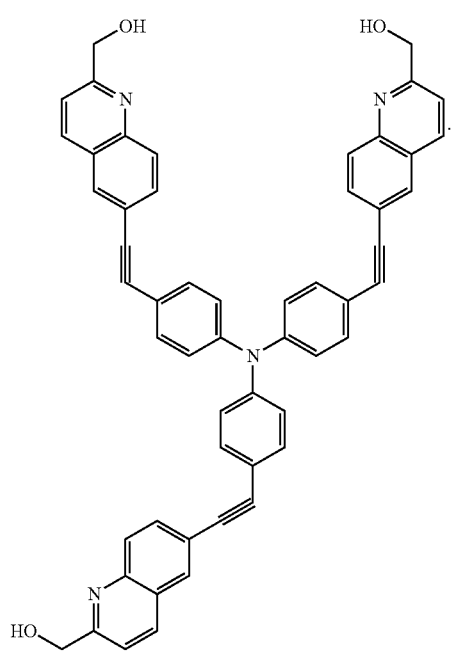
(I_F)

5. A method of synthesizing a compound according to claim 1, comprising the following steps:
  (i) a transformation step of an optionally substituted bromoaniline in a bromoquinaldine,
  (ii) an amination step of the bromoquinaldine obtained in step (i), in the presence of copper and L-proline,
  (iii) a reaction between the aminoquinaldine obtained in step (ii) and two equivalents of bromoquinaldine, and
  (iv) an oxidation step, followed by a reduction step.

6. An aqueous solution comprising at least one compound according to claim 1.

7. An aqueous solution according to claim 6, wherein the compound is present at a concentration ranging from $10^{-5}$ to $10^{-1}$ mol·$L^{-1}$.

8. An aqueous solution according to claim 6, having a pH of 6 to 8.

9. A method of liberating a Y—H, a Y'—H and/or a Y"—H compound, comprising the step of irradiating a compound according to claim 1.

10. A method as defined according to claim 9, wherein the irradiating step is carried out at a wavelength ranging from 600 to 1000 nm.

11. The method of claim 10, wherein the wavelength ranges from 650 to 800 nm.

* * * * *